(12) United States Patent
Sun et al.

(10) Patent No.: US 11,819,589 B2
(45) Date of Patent: *Nov. 21, 2023

(54) ABSORBABLE BIOMEDICAL POLYLACTIC ACID COMPOSITE MATERIAL AND PREPARATION METHOD THEREFOR

(71) Applicant: SHENZHEN CORLIBER SCIENTIFIC CO., LTD., Shenzhen (CN)

(72) Inventors: Yang Sun, Shenzhen (CN); Feng Pan, Shenzhen (CN); Yucheng Huang, Shenzhen (CN); Dong Xiang, Shenzhen (CN)

(73) Assignee: SHENZHEN CORLIBER SCIENTIFIC CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,643

(22) Filed: Mar. 26, 2022

(65) Prior Publication Data

US 2022/0226541 A1   Jul. 21, 2022

Related U.S. Application Data

(63) Continuation of application No. 16/615,133, filed as application No. PCT/CN2018/095731 on Jul. 15, 2018, now Pat. No. 11,311,651.

(30) Foreign Application Priority Data

Jul. 15, 2017 (CN) .......................... 201710578058.8
Jul. 15, 2017 (CN) .......................... 201710578059.2

(51) Int. Cl.
  *A61L 27/46*  (2006.01)
  *A61L 27/48*  (2006.01)
  *A61L 27/58*  (2006.01)

(52) U.S. Cl.
  CPC ............... *A61L 27/46* (2013.01); *A61L 27/48* (2013.01); *A61L 27/58* (2013.01)

(58) Field of Classification Search
  CPC .......... A61L 27/46; A61L 27/48; A61L 27/58
  See application file for complete search history.

(56) References Cited

U.S. PATENT DOCUMENTS

2013/0280335 A1* 10/2013 Han ........................ A61L 27/34
                                                              977/773

FOREIGN PATENT DOCUMENTS

CN           1544524         * 11/2004

* cited by examiner

*Primary Examiner* — Jianfeng Song
(74) *Attorney, Agent, or Firm* — AVEK IP, LLC

(57) ABSTRACT

The present invention relates to an absorbable biomedical composite material and a preparation method therefor, wherein the absorbable biomedical composite material comprises: a substrate particle containing a calcium phosphate compound; an intermediate layer which is coated on the surfaces of the substrate particle and has a first glass transition temperature, the first glass transition temperature being not higher than a normal body temperature; and a polymer matrix which is formed on the outer surface of the intermediate layer and has a second glass transition temperature, the second glass transition being higher than the first glass transition temperature. The present invention can provide an absorbable biomedical composite material which not only increases the mechanical strength but also improves the toughness.

11 Claims, 6 Drawing Sheets

ABSORBABLE BIOMEDICAL POLYLACTIC ACID COMPOSITE MATERIAL AND PREPARATION METHOD THEREFOR

CROSS REFERENCE TO RELATED APPLICATIONS

This application is a continuation of U.S. application Ser. No. 16/615,133, filed on Nov. 20, 2019, which is a National Stage Entry of PCT/CN2018/095731, filed on Jul. 15, 2018, which claims priority to Chinese application number 201710578058.8, filed on Jul. 15, 2017, and Chinese application number 201710578059.2, filed on Jul. 15, 2017, the disclosure of which are incorporated by reference herein in their entireties.

FIELD OF THE DISCLOSURE

The present invention relates to the field of biomedical composite materials, and more particularly relates to an absorbable biomedical composite material and a preparation method therefor.

BACKGROUND

The human bone contains water, organic matters (bone glue), inorganic salts and the like, wherein the inorganic salts are mainly composed of calcium phosphate compounds, which are distributed in the organic matters in the forms of crystalline hydroxyapatite and amorphous calcium phosphate. Therefore, inorganic salts containing calcium phosphate compounds, especially hydroxyapatite, calcium phosphate, etc., have excellent biocompatibility and bioactivity similar to those of inorganic salts of human bones. Biodegradable polyester materials, such as polylactic acid, polycaprolactone, polyglycolide, etc., which have good biodegradability, biocompatibility and mechanical properties, are common absorbable medical polymer materials and are widely applied in the medical field. A composite material prepared by combining inorganic salts containing calcium phosphate compounds with a bioabsorbable polyester material can integrate the advantages of the two materials, and has good biocompatibility, bioactivity and mechanical properties when used as bone fixation and bone repair materials.

However, the inorganic salts containing calcium phosphate compounds are mostly hydrophilic, and when they are simply blended with absorbable polyester materials, the interfaces therebetween have poor compatibility and lack an interfacial interaction force of a certain strength, so that inorganic salt particles are aggregated and thus unevenly dispersed in a polyester material matrix, easily resulting in stress concentration and cracks at the interfaces caused by dropping of the matrix and filler, which seriously affects the mechanical properties of the composite material. In addition, the addition of inorganic salt particles generally impairs the toughness of the polyester material, easily leading to brittle fracture, and limits the application of the composite material in the field of orthopedics. Therefore, orthopedic medical appliances made of ordinary polyesters and inorganic salt composite materials containing calcium phosphate compounds can bring a high risk to patients in practical applications.

In view of the above problems, the Patent Document 1 proposes a hydroxyapatite/polylactic acid composite material. Therein, the surface of the hydroxyapatite is modified by adsorbing low molecular weight polylactic acid. However, although the binding force between the modified hydroxyapatite and the polylactic acid matrix material is enhanced, it still lacks a strong interfacial force, and therefore, the mechanical properties of the resulting composite material still need to be improved.

Further, the Patent Document 2 also proposes a hydroxyapatite/polylactic acid composite material. Therein, this material is mainly made of hydroxyapatite and polylactic acid which are polymerized in situ, that is, there are covalent bonds between the hydroxyapatite and the polylactic acid. Although this can contribute greatly to the dispersion of hydroxyapatite, improve the interfacial interaction force and improve the mechanical properties of the material, in the hydroxyapatite/polylactic acid composite material, since there is no buffering mechanism between the rigid hydroxyapatite particles and the polylactic acid, the toughness of the composite material is easily damaged, and brittle fracture is prone to occur, which is disadvantageous in the application of the composite material in orthopedic clinics.

Further, in the Patent Document 3, a plurality of composite fibers are adopted to reinforce Poly(DL-lactide) wherein the composite fibers include calcium polyphosphate and hydroxyapatite, calcium carbonate or zirconium oxide, whereby the strength of the composite material is greatly improved. However, since there is no strong interfacial interaction force between the composite fibers and the Poly(DL-lactide), the strength of the composite material is not significantly improved, and the toughness of the composite material is also easily damaged.

PRIOR ART DOCUMENTS

Patent Documents

Patent Document 1: Chinese Granted Patent CN102153058B

Patent Document 2: Chinese Granted Patent CN103319696B

Patent Document 3: Chinese Published Patent Application CN1537892A

SUMMARY

The present invention is implemented in view of the above-described conditions of the prior art, and aims to provide an absorbable biomedical composite material which can not only increase the mechanical strength but also improve the toughness For this, the first aspect of the present invention provides an absorbable biomedical composite material comprising: a substrate particle containing a calcium phosphate compound; an intermediate layer which is coated on the surfaces of the substrate particle and has a first glass transition temperature, the first glass transition temperature being not higher than a normal body temperature; and a polymer matrix which is formed on the outer surface of the intermediate layer and has a second glass transition temperature, the second glass transition being higher than the first glass transition temperature.

In the first aspect of the present invention, the intermediate layer exists between the substrate particle and the polymer matrix, the glass transition temperature of the intermediate layer is not higher than the normal human body temperature, and therefore, when the composite material of the present invention is applied to orthopedic clinical treatment, the intermediate layer can be maintained in a rubbery state (highly elastic state) in the human body, and the intermediate layer in the rubbery state can release the stress concentration caused by the substrate particle and alleviate microcracks thereof, thereby improving the toughness of the composite material. In addition, the substrate particle can also suppress the severe deformation of the intermediate layer in the rubbery state under a certain stress, thereby being capable of suppressing the decrease in the strength of the composite material due to the addition of the material of the intermediate layer. in the rubbery state.

Further, in the composite material according to the first aspect of the present invention, optionally, the substrate particle contains one or more selected from the group consisting of hydroxyapatite, calcium polyphosphate, and tricalcium phosphate. In this case, since the constituents of the substrate particle are similar to the constituents of human bone tissues, the bioactivity and biocompatibility of the composite material can be improved.

Further, in the composite material according to the first aspect of the present invention, optionally, the substrate particle is rigid particle. Therefore, the mechanical strength of the composite material can be improved.

Further, in the composite material according to the first aspect of the present invention, optionally, the intermediate layer is a polymer layer, and the substrate particle and the intermediate layer are bonded via covalent bonds. In this case, a strong interfacial interaction force can be formed between the substrate particle and the intermediate layer, thereby effectively improving the bonding force therebetween and facilitating the force transmission.

Further, in the composite material according to the first aspect of the present invention, optionally, the mass percentage of the substrate particle is 1 wt % to 10 wt %, and the mass percentage of the intermediate layer is 1 wt % to 10 wt %. In this case, the mechanical strength of the composite material can be improved, and meanwhile other properties such as the toughness of the composite material are not affected or less affected.

Further, in the composite material according to the first aspect of the present invention, optionally, the polymer matrix is formed on the intermediate layer in an in-situ polymerization manner. In this case, a strong interfacial interaction force such as covalent bonds can be formed between the intermediate layer and the polymer matrix, thereby effectively improving the bonding force therebetween and facilitating the force transmission.

Further, in the composite material according to the first aspect of the present invention, optionally, the intermediate layer contains a homopolymer of a monomer selected from p-dioxanone or caprolactone, or a binary or higher order random copolymer or block copolymer selected from the group consisting of lactide, caprolactone, p-dioxanone, and glycolide. In this case, the intermediate layer can form an absorbable polymer material, which facilitates the application of the composite material in the field of orthopedics, particularly in the field of absorbable orthopedic materials.

Further, in the composite material according to the first aspect of the present invention, optionally, the intermediate layer is bonded to the polymer matrix via covalent bonds. In this case, a strong interfacial interaction force can be formed between the intermediate layer and the polymer matrix, thereby effectively improving the bonding force therebetween and facilitating the force transmission.

The second aspect of the present invention provides a preparation method for an absorbable biomedical composite material, the preparation method comprising: preparing a substrate particle composed of a calcium phosphate compound; sufficiently mixing the substrate particle with a first reactive monomer to obtain a mixed solution; adding a catalyst to the mixed solution, and heating to 80° C. to 180° C. in the presence of inert gas, and reacting for 2 hours to 48 hours, such that an intermediate layer composed of the first reactive monomer is coated on the substrate particle; and adding a second reactive monomer, maintaining heating, and continuing to react for 2 hours to 48 hours to form a polymer matrix on the intermediate layer. In this case, a composite material containing the intermediate layer can be formed, and the mechanical strength and toughness of the composite material can be improved, which is of great significance in the application of orthopedic medical appliances.

Further, in the preparation method for the composite material according to the second aspect of the present invention, optionally, the first reactive monomer and the second reactive monomer are respectively selected from at least one of lactide, caprolactone, p-dioxanone, and glycolide. In this case, an absorbable intermediate layer and a polymer matrix can be prepared, which facilitates the application of the composite material in the field of orthopedics, particularly in the field of absorbable orthopedic materials.

Further, in the preparation method for the composite material according to the second aspect of the present invention, optionally, the first reactive monomer is different from the second reactive monomer. In this case, the glass transition temperature of the intermediate layer or the polymer matrix can be controlled by adjusting the monomer type, monomer mass or monomer ratio and the like, which facilitates the application of the composite material in the field of orthopedics.

According to the first and second aspects of the present invention, it is possible to provide an absorbable biomedical composite material having high mechanical strength and good toughness and a preparation method therefor. (an absorbable biomedical composite material having high mechanical strength and good toughness and a preparation method therefor can be provided.)

The third aspect of the present invention provides an absorbable biomedical polylactic acid composite material comprising: a core-shell structure including a substrate particle containing a calcium phosphate compound, an intermediate layer coated on the surfaces of the substrate particle and a polymer layer formed on the outer surface of the intermediate layer; and a polylactic acid matrix which forms a stereocomplex with the polymer layer of the core-shell structure and has a third glass transition temperature, wherein the intermediate layer has a fourth glass transition temperature which is not higher than a normal human body temperature, and the third glass transition temperature is higher than the fourth glass transition temperature.

In the third aspect of the present invention, the absorbable biomedical polylactic acid composite material comprises the core-shell structure and the polylactic acid matrix which forms a stereocomplex force with the core-shell structure, wherein the stereocomplex force greatly facilitates the force transmission between the polylactic acid matrix and the core-shell structure and is capable of further assisting in the dispersion of the core-shell structure in the polylactic acid matrix; and in the core-shell structure, the intermediate layer exists between the substrate particle and the polymer layer, and the glass transition temperature of the intermediate layer is not higher than the normal human body temperature, and therefore, when the composite material of the present invention is applied to orthopedic clinical treatment, the intermediate layer of the core-shell structure can be maintained in a rubbery state (highly elastic state) in the human body, and the intermediate layer in the rubbery state can alleviate the stress concentration and microcracks caused by the substrate particle, thereby improving the toughness of the composite material. Meanwhile, the substrate particle can also stabilize under a certain stress the severe deformation of the intermediate layer in the rubbery state, thereby being capable of suppressing the decrease in the strength of the composite material.

Further, in the polylactic acid composite material according to the third aspect of the present invention, optionally, the substrate particle contain one or more selected from the group consisting of hydroxyapatite, calcium polyphosphate, and tricalcium phosphate. In this case, since the constituents of the substrate particle are similar to the constituents of human bone tissues, the bioactivity and biocompatibility of the polylactic acid composite material can be improved.

Further, in the polylactic acid composite material according to the third aspect of the present invention, optionally, the substrate particle is rigid particle. Therefore, the mechanical strength of the polylactic acid composite material can be improved.

Further, in the polylactic acid composite material according to the third aspect of the present invention, optionally, the mass percentage of the substrate particle is 1 wt % to 30 wt %. In this case, the mechanical strength of the polylactic acid composite material can be improved, and meanwhile other properties such as the toughness of the polylactic acid composite material are not affected or less affected.

Further, in the polylactic acid composite material according to the third aspect of the present invention, optionally, an average particle diameter of the substrate particle is 5 nm to 200 μm. In this case, the mechanical strength of the polylactic acid composite material can be improved, and other properties such as the toughness of the polylactic acid composite material are not affected or less affected.

Further, in the polylactic acid composite material according to the third aspect of the present invention, optionally, the intermediate layer contains a homopolymer of a monomer selected from one of p-dioxanone or caprolactone, or a binary or higher order random copolymer or block copolymer selected from the group consisting of lactide, caprolactone, p-dioxanone, and glycolide. In this case, the intermediate layer can form an absorbable polymer material, which facilitates the application of the composite material in the field of orthopedics, particularly in the field of absorbable orthopedic materials.

Further, in the polylactic acid composite material according to the third aspect of the present invention, optionally, the intermediate layer is composed of a polymer material, and the substrate particle are bonded to the intermediate layer via covalent bonds. In this case, a strong interfacial interaction force can be formed between the substrate particle and the intermediate layer, thereby effectively improving the bonding force therebetween and facilitating the force transmission.

Further, in the polylactic acid composite material according to the third aspect of the present invention, optionally, the polymer layer contains a homopolymer of a first type of lactide monomer, or a random copolymer or block copolymer of a first type of lactide and one or more monomers selected from the group consisting of a second type of lactide, caprolactone, p-dioxanone, and glycolide; the polylactic acid matrix contains a homopolymer of a second type of lactide monomer, or a random copolymer or block copolymer of a second type of lactide and one or more monomers selected from the group consisting of a first type of lactide, caprolactone, p-dioxanone, and glycolide, and the first type of lactide and the second type of lactide are levoisomer-dextroisomer of lactide for each other. In this case, the polymer layer and the polylactic acid matrix can form levoisomer and dextroisomer of polylactic acid respectively, and can function as special hydrogen bonds, that is, a stereocomplex force, which are more stable than common hydrogen bonds, thereby forming a stereocomplex when they are in contact. Therefore, the interfacial interaction force and stability of the polylactic acid composite material can be ensured.

Further, in the polylactic acid composite material according to the third aspect of the present invention, optionally, the stereocomplex crystallization ratio of the stereocomplex is 1% to 40%. In this case, the mechanical properties of the polylactic acid composite material can be effectively improved.

The fourth aspect of the present invention provides a preparation method for an absorbable biomedical polylactic acid composite material, the method comprising: preparing a substrate particle containing a calcium phosphate compound; sufficiently mixing the substrate particle with a third reactive monomer to obtain a mixed solution; adding a catalyst to the mixed solution, and heating to 80° C. to 180° C. in the presence of inert gas, and reacting for 2 hours to 48 hours, such that an intermediate layer composed of the third reactive monomer is coated on the substrate particle; adding a fourth reactive monomer, maintaining heating, and continuing to react for 2 hours to 48 hours to form a polymer layer on the intermediate layer, thereby obtaining a core-shell structure; and blending the core-shell structure and the polylactic acid matrix in a preset ratio to obtain a stereocomplex formed by the core-shell structure and the polylactic acid matrix. In this case, a polylactic acid composite material containing the core-shell structure and the polylactic acid matrix can be formed, and the mechanical strength and toughness of the composite material can be improved, which is of great significance in the application of orthopedic medical appliances.

Further, in the preparation method for the polylactic acid composite material according to the fourth aspect of the present invention, optionally, the polymer layer contains a homopolymer of a first type of lactide monomer, or a random copolymer or block copolymer of a first type of lactide and one or more monomers selected from the group consisting of a second type of lactide, caprolactone, p-dioxanone, and glycolide; the polylactic acid matrix contains a homopolymer of a second type of lactide monomer, or a random copolymer or block copolymer of a second type of lactide and one or more monomers selected from the group consisting of a first type of lactide, caprolactone, p-dioxanone, and glycolide, and the first type of lactide and the second type of lactide are levoisomer-dextroisomer of lactide for each other. In this case, the polymer layer and the polylactic acid matrix can form the levoisomer and the dextroisomer of the polylactic acid respectively, and can function as special hydrogen bonds, that is, a stereocomplex force, which are more stable than common hydrogen bonds, thereby forming a stereocomplex when they are in contact. Therefore, the interfacial interaction force and stability of the polylactic acid composite material can be ensured.

Further, in the preparation method for the polylactic acid composite material according to the fourth aspect of the present invention, optionally, the intermediate layer is composed of the polymer material, and the substrate particle are bonded to the intermediate layer via covalent bonds. In this case, a good bonding force between the substrate particles and the intermediate layer can be ensured, which facilitates the force transmission. According to the third and fourth aspects of the present invention, it is possible to provide an absorbable biomedical polylactic acid composite material having high mechanical strength and good toughness and a preparation method therefor.

BRIEF DESCRIPTION OF THE DRAWINGS

Illustrative embodiments of the present disclosure are described in detail below with reference to the figures.

Figure 1:
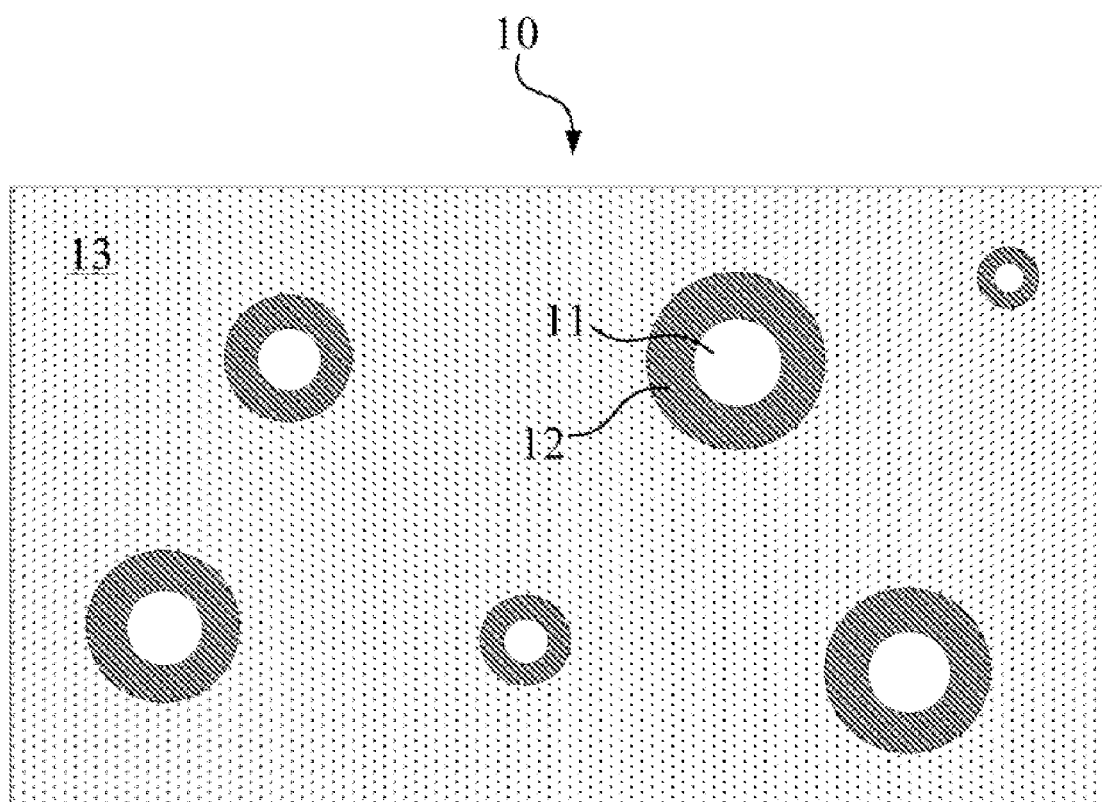
FIG. 1 is a schematic structure diagram showing an absorbable biomedical composite material according to a first embodiment of the present invention.

Reference numerals explanation: 10—composite material; 11—substrate particle; 12—intermediate layer; 13—polymer matrix; 2—polylactic acid composite material; 20—core-shell structure; 21—substrate particle; 22—intermeiate layer; 23—polymer layer; 30—polylactic acid matrix.

DETAILED DESCRIPTION

Hereinafter, preferred embodiments of the present invention will be described in detail with reference to the accompanying drawings. In the following description, the same components are denoted by the same reference numerals, and the description thereof will not be repeated. In addition, the drawings are merely schematic views, and the ratio of the dimensions of the components to each other or the shapes of the components can be different from the actual ones.

In addition, for the sake of description, the subtitles are used in the following description, but these subtitles merely serve as a hint for reading, and are not intended to limit the contents described under the subtitles to the subject of the subtitles.

First Embodiment

Composite Material

Figure 2:
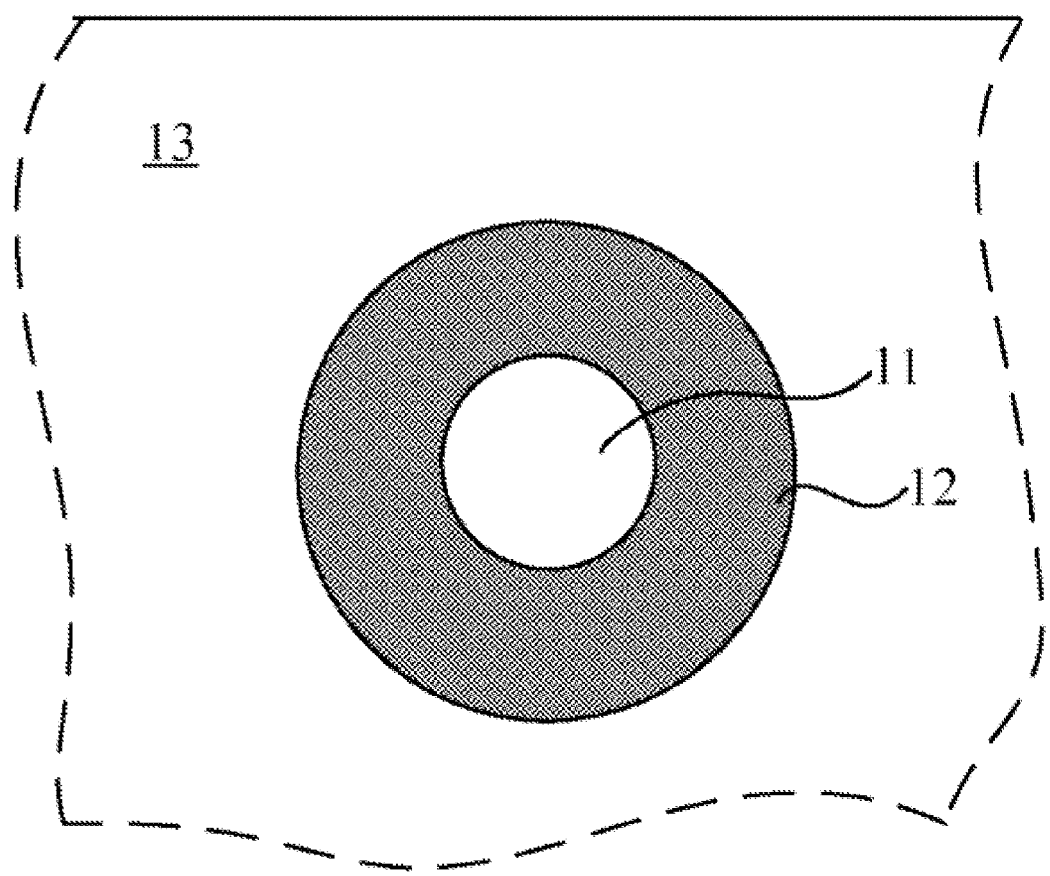
FIG. 2 is a partial structure schematic diagram showing the biomedical composite material according to the first embodiment of the present invention.

FIG. 1 is a schematic structure diagram showing an absorbable biomedical composite material according to a first embodiment of the present invention. FIG. 2 is a partial structure schematic diagram showing the biomedical composite material according to the first embodiment of the present invention.

As shown in FIGS. 1 and 2, the composite material 10 according to the first embodiment of the present invention can comprise substrate particle 11, an intermediate layer 12 and a polymer matrix 13. To be specific, the outer surfaces of the substrate particle 11 are coated with the intermediate layer 12, and the polymer matrix is formed on the outer surface of the intermediate layer 12. In some examples, the substrate particle 11 and the intermediate layer 12 can be uniformly dispersed as a whole in the polymer matrix 13.

As described above, the intermediate layer 12 is formed between the substrate particle 11 and the polymer matrix 13. In this case, a buffer mechanism is introduced between the substrate particle 11 and the polymer matrix 13, so that the interfacial interaction force between the substrate particle 11 and the polymer matrix 13 can be enhanced, and the dispersion of the substrate particle 11 in the polymer matrix 13 can be improved, thereby improving the mechanical strength and toughness of the composite material 1 simultaneously.

A Substrate Particle

In the present embodiment, the substrate particle 11 can contain a calcium phosphate compound. Preferably, the substrate particle 11 can contain one or more selected from the group consisting of hydroxyapatite, calcium polyphosphate, and tricalcium phosphate. In this case, the substrate particle 11 facilitates improving the bioactivity of the composite material 10 and promotes its repairing effect on human bone tissues.

It is well known that among inorganic constituents of human bone tissues, calcium phosphate compounds are dominant. After the composite material 10 according to the present embodiment is implanted into the body as an orthopedic repair material, the intermediate layer 12 and the polymer matrix 13 (described later) will be absorbed by the human body, and therefore, elements such as calcium and phosphorus contained in the substrate particle 11 are absorbed by body tissues to form new bone tissues, thereby contributing to bone growth and repair.

Further, the substrate particle 11 are not limited to the above-described hydroxyapatite, calcium polyphosphate, tricalcium phosphate or the like. In the present embodiment, the substrate particle 11 can improve the repairing effect of the composite material 10 on human bone tissues as long as the substrate particle 11 contain substances similar to the constituents of the human bone tissues.

In the present embodiment, preferably, the substrate particle 11 is rigid particle. In some examples, the substrate particle 11 can be rigid particle with Young's modulus greater than $2\times10^{11}$ Pa. In this case, the mechanical strength of the composite material 10 can be effectively improved.

Further, in the present embodiment, the shape of the substrate particle 11 is not particularly limited. For example, in some examples, the substrate particle 11 can be spherical. However, the present embodiment is not limited thereto, and in other examples, the substrate particle 11 can be ellipsoidal, irregularly stereoscopic, or the like.

In the present embodiment, the mass percentage (wt %) of the substrate particle 11 is not particularly limited. In view of the mechanical strength and toughness of the composite material 10, the mass percentage of the substrate particle 11 is preferably from 1 wt % to 10 wt %, for example, the mass percentage of the substrate particle 11 can be 1 wt %, 3 wt %, 5 wt %, 8 wt % or 10 wt %. Specifically, in the composite material 10, the substrate particle 11 function as improving the mechanical strength of the composite material 10, and generally, the more the content of the substrate particle 11, the higher the mechanical strength of the composite material 10. When the content of the substrate particle 11 is relatively low, the mechanical strength of the composite material 10 is insufficient, and when the content of the substrate particle 11 is excessive, the content of the polymer matrix 13 in the composite material 10 is relatively reduced, thereby affecting the mechanical strength of the composite material 10. Therefore, by taking the mass percentage of the substrate particle 11 at 1 wt % to 10 wt %, the mechanical strength of the composite material 10 can be improved, or the mechanical strength of the composite material 10 can be prevented from being affected or less affected.

Further, in the present embodiment, an average particle diameter of the substrate particle 11 is not particularly limited. In view of the mechanical strength and toughness of the composite material 10, the average particle diameter of the substrate particle 11 is preferably from 5 nm to 200 μm, for example, the average particle diameter of the substrate particle 11 can be 5 nm, 10 nm, 30 nm, 50 nm, 1 μm, 2 μm, 5 μm, 10 μm, 20 μm, 30 μm, 50 μm, 80 μm, 100 μm, 130 μm, 150 μm, 180 μm or 200 μm. Specifically, the smaller the particle diameter of the substrate particle 11 generally is, the stronger the rigidity thereof is. Therefore, when the substrate particle 11 with relatively small particle diameter is selected, the effect of the substrate particle 11 on the increase of the mechanical strength of the composite material 10 can be sufficiently exerted; as the particle size of the substrate particle 11 increases, the surface energy thereof is reduced, and agglomeration can be suppressed to some extent, but when the particle size of the substrate particle 11 is too large, the uniformity (homogeneity) of dispersion thereof will be affected, thereby affecting the mechanical strength of the polylactic acid composite material 1. Therefore, by limiting the particle diameter of the substrate particle 11 within the above range, not only the mechanical strength of the composite material 10 can be enhanced, but also the dispersion of the substrate particle 11 is kept uniformly enough.

An Intermediate Layer

In the present embodiment, the intermediate layer 12 can be coated on the surfaces of the substrate particle 11. That is, the intermediate layer 12 covers the surfaces of the substrate particle 11. Additionally, the intermediate layer 12 can have a first glass transition temperature T1. In some examples, the first glass transition temperature T1 can be not higher than a normal human body temperature. In general, for a glass transition temperature of a substance, when the external temperature is higher than a glass transition temperature of a polymer, the substance will be in an elastic state or a rubbery state; and when the external temperature is lower than or equal to the glass transition temperature of the polymer, the substance will be in a glassy state.

When the composite material 10 according to the present embodiment is applied to a human body, since the first glass transition temperature T1 of the intermediate layer 12 is not higher than the normal human body temperature (for example, 37° C.), the intermediate layer 12 can be maintained in a rubbery state. In this case, the intermediate layer in the rubbery state 12 can release (for example, release in situ) the stress concentration caused by the substrate particle 11 and alleviate the resulting microcracks, whereby the toughness of the composite material 10 can be improved. In addition, the substrate particle 11 can also stabilize (for example, stabilize in situ) the severe deformation of the intermediate layer 12 in the rubbery state under a certain stress, whereby the decrease in the mechanical strength of the composite material 10 can be suppressed.

In the present embodiment, the intermediate layer 12 can be composed of a polymer material, and the intermediate layer 12 can be bonded to the substrate particle 11 via covalent bonds. In this case, a strong interfacial interaction force is formed between the substrate particle 11 and the intermediate layer 12, thereby effectively improving the bonding force therebetween and facilitating the force transmission. In addition, the intermediate layer 12 can be bonded to the substrate particle 11 by a strong interfacial interaction force such as ionic bonds.

In the clinical application of human orthopedics repair, when there is a strong force between the intermediate layer 12 in the rubbery state and the substrate particle 11, it can contribute to the force transmission between the intermediate layer 12 and the substrate particle 11 and promote a linkage effect therebetween. To be specific, on the one hand, the intermediate layer 12 in the rubbery state can release (for example, release in situ) the stress concentration caused by the substrate particle 11 and alleviate the resulting microcracks, whereby the toughness of the composite material 10 can be improved; and on the other hand, the substrate particle 11 can also stabilize (for example, stabilize in situ) the severe deformation of the intermediate layer 12 in the rubbery state under a certain stress, whereby the decrease in the mechanical strength of the composite material 10 caused by the addition of the intermediate layer 12 in the rubbery state can be effectively suppressed. Therefore, the strength and toughness of the composite material 10 can be simultaneously improved, which is of great significance in the application of the composite material 10 of the present embodiment in orthopedic medical appliances.

In the present embodiment, the mass percentage (wt %) of the intermediate layer 12 is not particularly limited. In view of the mechanical strength and toughness of the composite material 10, the mass percentage of the intermediate layer 12 is preferably from 1 wt % to 10 wt %, for example, the mass percentage of the intermediate layer 12 can be 1 wt %, 3 wt %, 5 wt %, 8 wt % or 10 wt %. Specifically, in the composite material 10, the intermediate layer 12 functions as improving the toughness of the composite material 10, and generally, the more the content of the intermediate layer 12, the higher the toughness of the composite material 10. When the content of the intermediate layer 12 is relatively low, the toughness of the composite material 10 is insufficient, and when the content of the intermediate layer 12 is excessive, the performance features of the composite material 10, such as the mechanical strength will be affected. Therefore, by taking the mass percentage of the intermediate layer 12 at 1 wt % to 10 wt %, the toughness of the composite material 10 can be improved, and the mechanical strength and other performance features of the composite material 10 can be prevented from being affected or less affected.

In the present embodiment, the intermediate layer 12 can contain a homopolymer of a monomer selected from one of p-dioxanone and caprolactone. Moreover, the intermediate layer 12 can also contain a binary or higher order random copolymer or block copolymer selected from the group consisting of lactide, caprolactone, p-dioxanone, and glycolide. In this case, the intermediate layer 12 can form an absorbable polymer material, which facilitates the application of the composite material 10 in the field of orthopedics, especially in the field of absorbable orthopedic materials.

As described above, in the present embodiment, the first glass transition temperature T1 of the intermediate layer 12 can be not higher than the normal human body temperature. In addition, the specific numerical range of the first glass transition temperature T1 is not particularly limited. Preferably, the first glass transition temperature T1 satisfies $-40°$ C.$\leq T1 \leq 36°$ C., for example, the first glass transition temperature T1 can be $-40°$ C., $-37°$ C., $-30°$ C., $-20°$ C., $-10°$ C., −5° C., 0° C., 10° C., 20° C. or 36° C.; and more preferably, the first glass transition temperature T1 satisfies −37° C.≤T1≤36° C.

In addition, in the present embodiment, the magnitude of the glass transition temperature T1 of the intermediate layer 12 can be adjusted according to actual needs. For a homopolymer, different glass transition temperatures T1 can be obtained by adjusting the variety or mass of monomers thereof; for a copolymer, the glass transition temperature T1 can be changed by adjusting proportions of monomers thereof in mixed monomers.

Further, in the present embodiment, a molding method of the intermediate layer 12 is not particularly limited. In some examples, the intermediate layer can be formed by initiating in situ polymerization on the outer surfaces of the substrate particle 11. In addition, in other examples, the intermediate layer can also be formed by modifying the surfaces of the substrate particle 11.

Polymer Matrix

In the present embodiment, the polymer matrix 13 is formed on the outer surface of the intermediate layer 12. Additionally, the polymer matrix 13 can have a second glass transition temperature T2. In some examples, the second glass transition temperature T2 can be higher than the first glass transition temperature T1 of the intermediate layer 12, i.e., T2>T1. Thus, under the same temperature conditions, the polymer matrix 13 can maintain better mechanical strength than the intermediate layer 12, thereby enhancing the mechanical properties of the composite material 10.

In addition, in the present embodiment, the second glass transition temperature T2 of the polymer matrix 13 can be higher than the normal human body temperature. Thus, when the composite material 10 according to the present embodiment is applied to a human body, the polymer matrix 13 can be maintained in a glassy state, and the mechanical strength of the composite material 10 can be further ensured to be high enough.

In the present embodiment, the polymer matrix 13 can be formed on the intermediate layer 12 in an in-situ polymerization manner. In this case, a strong interfacial interaction force such as covalent bonds can be formed between the intermediate layer 12 and the polymer matrix 13, thereby effectively improving the bonding force therebetween and facilitating the force transmission.

In the present embodiment, the intermediate layer 12 can be bonded to the polymer matrix 13 via covalent bonds. In this case, a strong interfacial interaction force is formed between the intermediate layer 12 and the polymer matrix 13, thereby effectively increasing the bonding force therebetween and facilitating the force transmission. In addition, the intermediate layer 12 can also be bonded to the polymer matrix 13 by a strong interfacial interaction force such as ionic bonds.

Further, in the present embodiment, the polymer matrix 13 can contain a homopolymer of a monomer selected from the group consisting of lactide, caprolactone, p-dioxanone, and glycolide. Further, the polymer matrix 13 can also contain a binary or higher order random copolymer or block copolymer selected from the group consisting of lactide, caprolactone, p-dioxanone, and glycolide. In this case, the polymer matrix 13 can form an absorbable polymer material that facilitates the application of the composite material 10 in the field of orthopedics, particularly in the field of absorbable orthopedic materials.

Figure 3:
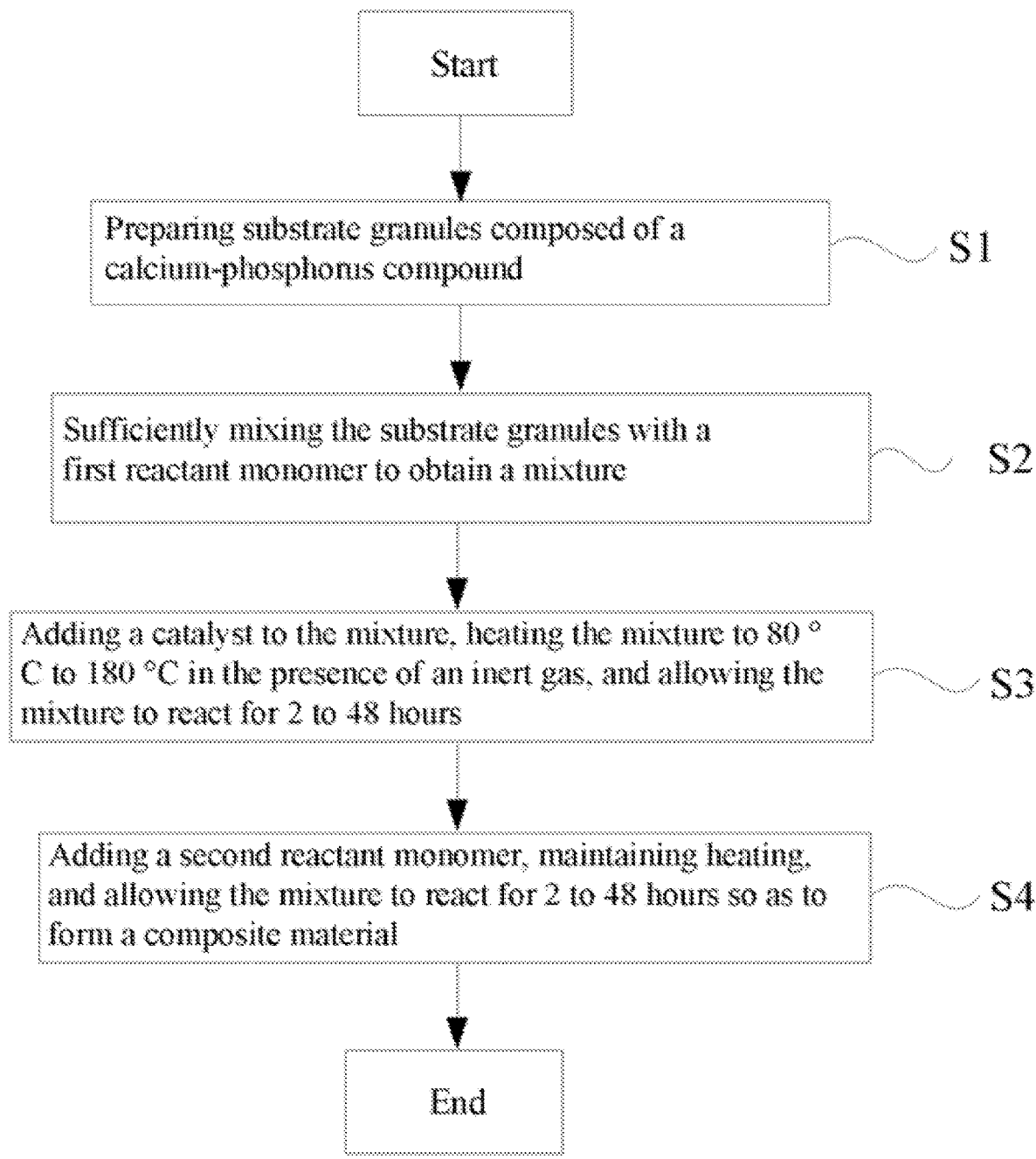
FIG. 3 is a schematic diagram showing the preparation steps of an absorbable biomedical composite material.

FIG. 3 is a schematic diagram showing the preparation steps of an absorbable biomedical composite material.

Hereinafter, a preparation method for the absorbable biomedical composite material according to the present embodiment will be described in detail with reference to FIG. 3.

As shown in FIG. 3, the preparation method for the absorbable biomedical composite material according to the present embodiment comprises the following steps: preparing substrate particle 11 composed of a calcium phosphate compound (step S1); sufficiently mixing the substrate particle 11 with a first reactive monomer to obtain a mixed solution (step S2); adding a catalyst to the mixed solution, and heating to 80° C. to 180° C. in the presence of inert gas, and reacting for 2 hours to 48 hours, such that an intermediate layer 12 composed of the first reactive monomer is coated on the substrate particle 11 (step S3); and adding a second reactive monomer, maintaining heating, and continuing to react for 2 hours to 48 hours to form a polymer matrix 13 on the intermediate layer 12 to finally obtain the composite material 10 (step S4).

In the present embodiment, in step S1, the substrate particle 11 composed of the calcium phosphate compound is first prepared. In some examples, the substrate particle 11 can be selected from one or more of the group consisting of hydroxyapatite, calcium polyphosphate, and tricalcium phosphate. It is well known that among inorganic constituents of human bone tissues, calcium phosphate compounds are dominant. After the composite material 10 according to the present embodiment is implanted into the body as an orthopedic repair material, the intermediate layer 12 and the polymer matrix 13 (described later) will be absorbed by the human body, and therefore, elements such as calcium and phosphorus contained in the substrate particle 11 are absorbed by body tissues to form new bone tissues, thereby contributing to bone growth and repair.

Further, the substrate particle 11 is not limited to the above-described hydroxyapatite, calcium polyphosphate, tricalcium phosphate or the like. In the present embodiment, the substrate particle 11 can also improve the repairing effect of the composite material 10 on the human bone tissues as long as the substrate particle 11 contains substances similar to the constituents of the human bone tissues.

In the present embodiment, in step S2, the substrate particle 11 in the step S1 can be sufficiently mixed with the first reactive monomer to obtain the mixed solution. In some examples, in step S2, the substrate particle 11 and the first reactive monomer can be simultaneously dissolved in an organic solvent and thoroughly mixed to form the mixed solution. In other examples, the organic solvent is preferably dry toluene.

Therein, the first reactive monomer can be selected one from the group consisting of lactide, caprolactone, p-dioxanone, and glycolide. Further, the first reactive monomer can be selected two or more from the group consisting of lactide, caprolactone, p-dioxanone, and glycolide. In this case, the resulting intermediate layer 12 is a homopolymer containing a monomer selected from p-dioxanone and caprolactone, or is a binary or higher order random copolymer or block copolymer selected from the group consisting of lactide, caprolactone, p-dioxanone, and glycolide. Thus, the intermediate layer 12 can form an absorbable polymeric material that facilitates the application of the composite material 10 in the field of orthopedics, particularly in the field of absorbable orthopedic materials.

Further, in the present embodiment, in the step S2, the process of adding the first reactive monomer can contain one or more additions. In some examples, the next addition is carried out after a reaction is performed for a certain period of time after each addition, whereby a block polymer can be formed.

In the present embodiment, in step S3, the catalyst is added to the mixed solution obtained in step S2, and heated to 80° C. to 180° C. in the presence of inert gas, and the reaction is performed for 2 hours to 48 hours, such that the intermediate layer 12 composed of the first reactive monomer is coated on the substrate particle 11. In some examples, there is a strong force, such as covalent bonds between the substrate particle 11 and the intermediate layer 12, and therefore the bonding force therebetween can be improved to facilitate the construction of force and promote a linkage effect therebetween.

Further, in the present embodiment, in step S3, the catalyst is preferably stannous octoate. Therefore, in-situ polymerization of monomers can be initiated to form a strong interfacial interaction force such as covalent bonds.

Further, in the present embodiment, in step S3, the inert gas can be nitrogen gas or argon gas. Therefore, the success occurrence of the reaction can be ensured, and the formation of other impurities can be effectively avoided.

In the present embodiment, in step S4, in the reaction system of step S3, the second reactive monomer is added, heating is maintained, and the reaction is continued for 2 hours to 48 hours, thereby forming a polymer matrix 13 on the intermediate layer 12 and finally obtaining the composite material 10.

Therein, the second reactive monomer can be selected from one of lactide, caprolactone, p-dioxanone, and glycolide. Further, the second reactive monomer can be selected from two or more of lactide, caprolactone, p-dioxanone, and glycolide. In this case, the resulting polymer matrix 13 is a homopolymer containing a monomer selected from the group consisting of lactide, caprolactone, p-dioxanone, and glycolide, or is a binary or higher order random copolymer or block copolymer selected from the group consisting of lactide, caprolactone, p-dioxanone, and glycolide. Thus, the polymer matrix 13 can form an absorbable polymer material that facilitates the application of the composite material 10 in the field of orthopedics, particularly in the field of absorbable orthopedic materials.

In some examples, the second reactive monomer can be different from the first reactive monomer. The differences include different types, different contents, or different types and contents.

Further, in the present embodiment, in the step S4, the process of adding the second reactive monomer can contain one or more additions. In some examples, the next addition is carried out after a reaction is performed for a certain period of time after each addition, whereby a block polymer can be formed.

Further, in the present embodiment, the products of the two stages of step S3 and step S4 are respectively dissolved in a first organic solvent, and preferably, the first organic solvent is chloroform. Then, after centrifuging, the products are precipitated in a second organic solvent and washed, and preferably, the second organic solvent is methanol, and an intermediate layer 12 polymer (the intermediate layer 12), a composition of the substrate particle 11 and the intermediate layer 12 (substrate particle 11-intermediate layer 12), and a composite material 10 (substrate particle 11-intermediate layer 12-polymer matrix 13) containing the substrate particle 11, the intermediate layer 12 and the polymer matrix 13 can be finally obtained.

In addition, in the present embodiment, a glass transition temperature of the material can be tested by differential scanning calorimetry (DSC), a weight-average molecular weight (Mw) of the material can also be obtained by gel permeation chromatography (GPC), and the component content of the material can be measured by thermogravimetric analysis (TGA).

In addition, in the present embodiment, the composite material 10 obtained in the step S4 is subjected to injection molding, and the mechanical property analysis result of the composite material 10 is obtained by testing.

In the present embodiment, the absorbable biomedical composite material 10 prepared by the steps S1 to S4 comprises the substrate particle 11 and the polymer matrix 13, and the intermediate layer 12 interposed between the substrate particle 11 and the polymer matrix 13. As described above, the glass transition temperature of the intermediate layer 12 is not higher than the normal human body temperature, and therefore, when the composite material 10 according to the present embodiment is applied to orthopedic clinic treatment, the intermediate layer 12 can be maintained in a rubbery state in the human body, such that the intermediate layer 12 in the rubbery state can alleviate the stress concentration and microcracks caused by the substrate particle 11, whereby the toughness of the composite material 10 can be improved. Meanwhile, the substrate particle 11 can also stabilize the severe deformation of the intermediate layer 12 in the rubbery state under a certain stress, whereby the decrease in the mechanical strength of the composite material 10 can also be suppressed.

In order to further describe the present invention, the absorbable biomedical composite material and the preparation method therefor provided by the present invention are described in detail below with reference to the examples, and the beneficial effects achieved by the present invention are fully described in conjunction with the comparative examples.

EXAMPLE 1

0.1 g of hydroxyapatite having a particle diameter of 5 nm, 0.06 g of L-lactide monomer and 0.06 g of caprolactone monomer were uniformly mixed; 40 µl of stannous octoate was added, and then heated with stirring to 180° C. in the presence of nitrogen gas; the reaction mixture continued to be reacted with stirring for 2 hours after being uniformly melted, to form a hydroxyapatite-rubbery layer. Then, 10 g of L-lactide was added to the reaction system, and the reaction was continued at 180° C. for 2 hours.

After completion of the reaction, the reaction mixture was dissolved in chloroform, then precipitated in methanol, and washed for three times with methanol to obtain a hydroxyapatite-rubbery layer-polylactic acid composite material.

The obtained hydroxyapatite-rubbery layer composite material and hydroxyapatite-rubbery layer-polylactic acid composite material were respectively dissolved in chloroform, and then centrifuged at a rate of 15000 rpm, and supernatant liquid was precipitated in methanol and washed to obtain a free rubbery polymer and a rubbery layer-polylactic acid polymer for material characterization. Differential scanning calorimetry (DSC) and gel permeation chromatography (GPC) data are shown in Table 1.

TABLE 1

| Sample | | Glass transition temperature (Tg, °C) | Weight-average molecular weight (Mw, g/mol) | Content of rubbery layer (wt %) |
|---|---|---|---|---|
| Example 1 | Rubbery layer | −7 | 3,000 | — |
| | Rubbery layer-polylactic acid | 52 | 305,000 | 0.96 |
| Example 2 | Rubbery layer | 25 | 5,000 | — |
| | Rubbery layer-polyglycolide | 40 | 40,300 | 9.93 |
| Example 3 | Rubbery layer | −37 | 4,500 | — |
| | Rubbery layer-poly(lactic acid-glycolic acid) | 45 | 86,000 | 4.72 |
| Comparative Example 1 | Polylactic acid | 55 | 320,000 | — |
| Comparative Example 2 | Polylactic acid | 56 | 331,000 | — |

The hydroxyapatite-rubbery layer-polylactic acid composite material was subjected to injection molding, and the tensile mechanical property test results are shown in Table 2. The mass content of hydroxyapatite in the hydroxyapatite-rubbery layer-polylactic acid composite material is determined by TGA and is 1%. The mass content of the rubbery layer in the hydroxyapatite-rubbery layer-polylactic acid composite material is calculated from the weight-average molecular weight of the rubbery layer and the rubbery layer-polylactic acid in Table 1, and in combination with the content of hydroxyapatite. The results are shown in Table 1.

TABLE 2

| Sample | | Young's modulus (GPa) | Tensile strength (MPa) | Elongation at break (%) |
|---|---|---|---|---|
| Example 1 | Hydroxyapatite-rubbery layer-polylactic acid | 4.1 | 45.2 | 15.1 |
| Example 2 | Hydroxyapatite-rubbery layer-polyglycolide | 3.0 | 35.3 | 30.2 |
| Example 3 | Hydroxyapatite-rubbery layer-poly(lactic acid-glycolic acid) | 3.5 | 38.5 | 21.3 |
| Comparative Example 1 | Hydroxyapatite-polylactic acid | 5.5 | 60.2 | 2.1 |
| Comparative Example 2 | Hydroxyapatite/polylactic acid | 4.2 | 48.1 | 2.2 |
| Comparative example 3 | Polylactic acid | 3.5 | 40.1 | 6.1 |

EXAMPLE 2

1 g of hydroxyapatite having a particle diameter of 200 um, 0.4 g of L-lactide monomer, 0.4 g of p-dioxanone monomer and 0.4 g of glycolide monomer were uniformly mixed in 100 ml of dry toluene; 160 μl of stannous octoate was added, and then heated with stirring to 80° C. in the presence of argon gas; the reactant was mixed and dissolved uniformly, and then continues to be reacted with stirring for 48 hours, to form a hydroxyapatite-rubbery layer. Then, 8.5 g of glycolide was added to the reaction system, and the reaction was continued at 80° C. for 48 hours.

After completion of the reaction, the reaction mixture was precipitated in methanol, and washed for three times with methanol to obtain a hydroxyapatite-rubbery layer-polyglycolide composite material.

The obtained hydroxyapatite-rubbery layer composite material and hydroxyapatite-rubbery layer-polyglycolide composite material were respectively dissolved in chloroform, and then centrifuged at a rate of 15,000 rpm, and supernatant liquid was precipitated in methanol and washed to obtain a free rubbery polymer and a rubbery-polyglycolide polymer for material characterization. Differential scanning calorimetry (DSC) and gel permeation chromatography (GPC) data are shown in Table 1.

The hydroxyapatite-rubbery layer-polyglycolide composite material was subjected to injection molding, and the tensile mechanical property test results are shown in Table 2. The mass content of hydroxyapatite in the hydroxyapatite-rubbery layer-polyglycolide composite material is determined by TGA and is 10%. The mass content of the rubbery layer in the hydroxyapatite-rubbery layer-polyglycolide composite material is calculated from the weight-average molecular weight of the rubbery layer and the rubbery layer-polylactic acid in Table 1, and in combination with the content of hydroxyapatite. The results are shown in Table 1.

EXAMPLE 3

0.5 g of hydroxyapatite having a particle diameter of 200 nm and 0.3 g of caprolactone monomer were uniformly mixed in 100 ml of dry toluene; 100 μl of stannous octoate was added, and then heated with stirring to 120° C. in the presence of argon gas; the reactant was mixed and dissolved uniformly, and then continues to be reacted with stirring for 12 hours; then 0.3 g of p-dioxanone monomer was added, and the reaction was continued at 120° C. for 12 hours to form a hydroxyapatite-rubbery layer. Then, 4.6 g of glycolide was added to the reaction system, and the reaction was continued at 130° C. for 24 hours; 4.6 g of L-lactide was then added, and the reaction was continued at 130° C. for 24 hours.

After completion of the reaction, the reaction mixture was precipitated in methanol, and washed for three times with methanol to obtain a hydroxyapatite-rubbery layer-poly(lactic acid-glycolic acid) composite material.

The obtained hydroxyapatite-rubbery layer composite material and hydroxyapatite-rubbery layer-poly(lactic acid-glycolic acid) composite material were respectively dissolved in chloroform, and then centrifuged at a rate of 15,000 rpm, and supernatant liquid was precipitated in methanol and washed to obtain a free rubbery polymer and a rubbery layer-poly(lactic acid-glycolic acid) polymer for material characterization. Differential scanning calorimetry (DSC) and gel permeation chromatography (GPC) data are shown in Table 1.

The hydroxyapatite-rubbery layer-poly(lactic acid-glycolic acid) composite material was subjected to injection molding, and the tensile mechanical property test results are shown in Table 2. The mass content of the hydroxyapatite in the hydroxyapatite-rubbery layer-poly(lactic acid-glycolic acid) composite material is determined by TGA and is 5%. The mass content of the rubbery layer in the hydroxyapatite-rubbery layer-poly(lactic acid-glycolic acid) composite material is calculated from the weight-average molecular weight of the rubbery layer and the rubbery layer-polylactic acid in Table 1, and in combination with the content of hydroxyapatite. The results are shown in Table 1.

Comparative Example 1

0.1 g of hydroxyapatite having a particle diameter of 5 nm and 10 g of L-lactide monomer were uniformly mixed; 40 μl of stannous octoate was added, and then heated with stirring to 180° C. in the presence of nitrogen gas; the reaction mixture continues to be reacted with stirring for 2 hours after being uniformly melted, to form a hydroxyapatite-polylactic acid composite material.

After completion of the reaction, the reaction mixture was dissolved in chloroform and then precipitated in methanol, and washed for three times with methanol to obtain a hydroxyapatite-polylactic acid composite material.

The obtained hydroxyapatite-polylactic acid composite material was dissolved in chloroform, and then centrifuged at a rate of 15,000 rpm, and supernatant liquid was precipitated in methanol and washed to obtain a free polylactic acid for material characterization. Differential scanning calorimetry (DSC) and gel permeation chromatography (GPC) data are shown in Table 1.

The hydroxyapatite-polylactic acid composite material was subjected to injection molding, and the tensile mechanical property test results are shown in Table 2. The mass content of the hydroxyapatite in the hydroxyapatite-polylactic acid composite material is determined by TGA and is 1%.

Comparative Example 2

0.1 g of hydroxyapatite having a particle diameter of 5 nm and 9.9 g of L-polylactic acid were dispersed and dissolved in chloroform, stirred uniformly, and then precipitated in methanol to obtain a hydroxyapatite/polylactic acid composite material.

The molecular weight and the glass transition temperature of the L-polylactic acid used in this comparative example are close to those of Comparative Example 1, and the data results of differential scanning calorimetry (DSC) and gel permeation chromatography (GPC) are shown in Table 1. The hydroxyapatite/polylactic acid composite material was subjected to injection molding, and the tensile mechanical property test results are shown in Table 2. The mass content of the hydroxyapatite in the hydroxyapatite/polylactic acid composite material is determined by TGA and is 1.2%.

Comparative Example 3

The L-polylactic acid in Comparative Example 2 was subjected to injection-molding, and the tensile mechanical property test results are shown in Table 2.

As can be seen from the comparison of Example 1 and Comparative Example 3, the interface design method of the present invention can effectively and simultaneously increase the strength (represented by Young's modulus and tensile strength) and toughness (represented by elongation at break) of a polyester material.

As can be seen from the comparison of Example 1 and Comparative Example 1, a cushion effect of the rubbery layer between the hydroxyapatite and the polylactic acid is helpful for improving the toughness of the polylactic acid material.

In Comparative Example 2, there was no strong interfacial interaction force between the hydroxyapatite and the polylactic acid matrix, so as can be seen from the comparison of Example 1, Comparative Example 1 and Comparative Example 2, a strong force at the interface in the absorbable composite material of the present invention plays an important role in improving the mechanical properties of the composite material.

Second Embodiment

Polylactic Acid Composite Material

Figure 4:
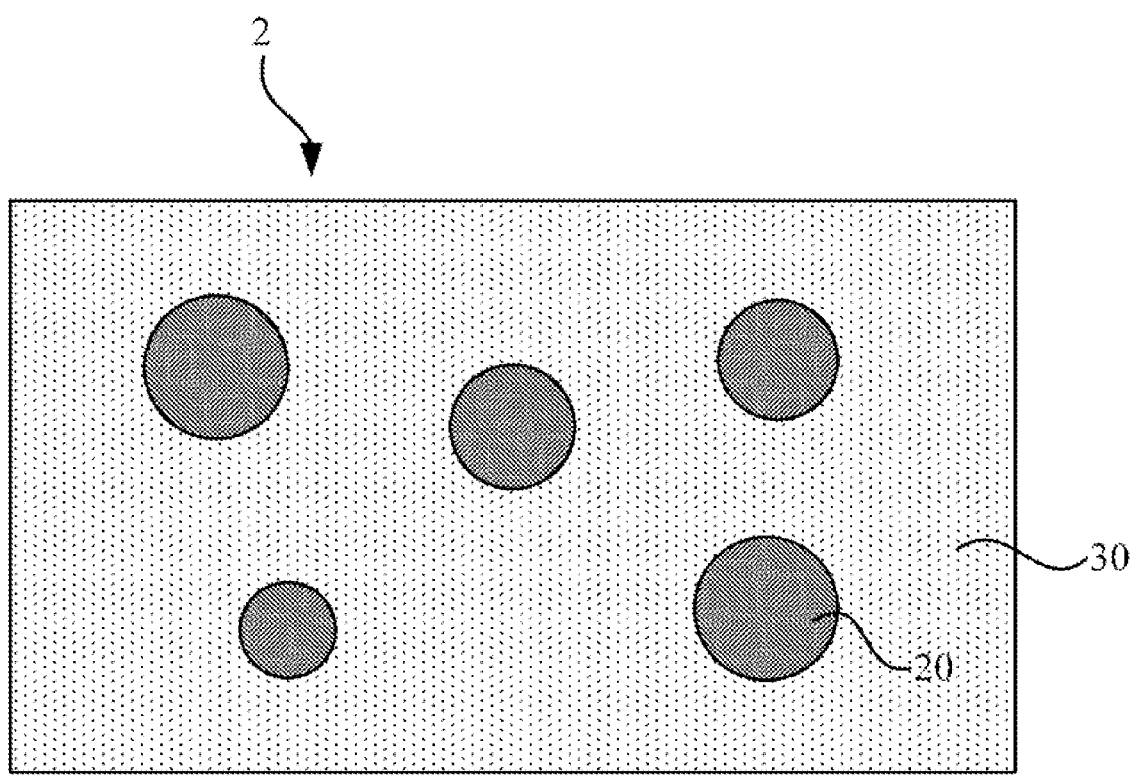
FIG. 4 is a schematic structural diagram showing an absorbable biomedical polylactic acid composite material according to a second embodiment of the present invention.

FIG. 4 is a schematic structural diagram showing an absorbable biomedical polylactic acid composite material according to a second embodiment of the present invention.

As shown in FIG. 4, the polylactic acid composite material 2 according to the present embodiment can comprise a core-shell structure 20 and a polylactic acid matrix 30. Therein, in some examples, the core-shell structure 20 can be distributed in the polylactic acid matrix 30. Further, the polylactic acid matrix 30 can form a stereocomplex with the core-shell structure 20, that is, the polylactic acid matrix 30 and the core-shell structure 20 can be combined by a stereocomplex force, and therefore, the interfacial interaction force and stability of the polylactic acid composite material 2 can be effectively ensured.

The absorbable biomedical polylactic acid composite material 2 according to the present embodiment is particularly suitable for use in the field of orthopedic treatment. For example, the polylactic acid composite material 2 according to the present embodiment can be used as an orthopedic implant material to repair bones of a human body. The polylactic acid composite material 2 according to the present embodiment has excellent bioactivity on the one hand and can promote growth and repair of bone tissues, and on the other hand, the material can be absorbed by the human body, and is metabolized and absorbed by the human body, thereby being favored in the field of orthopedic clinical application.

Core-Shell Structure

Figure 5:
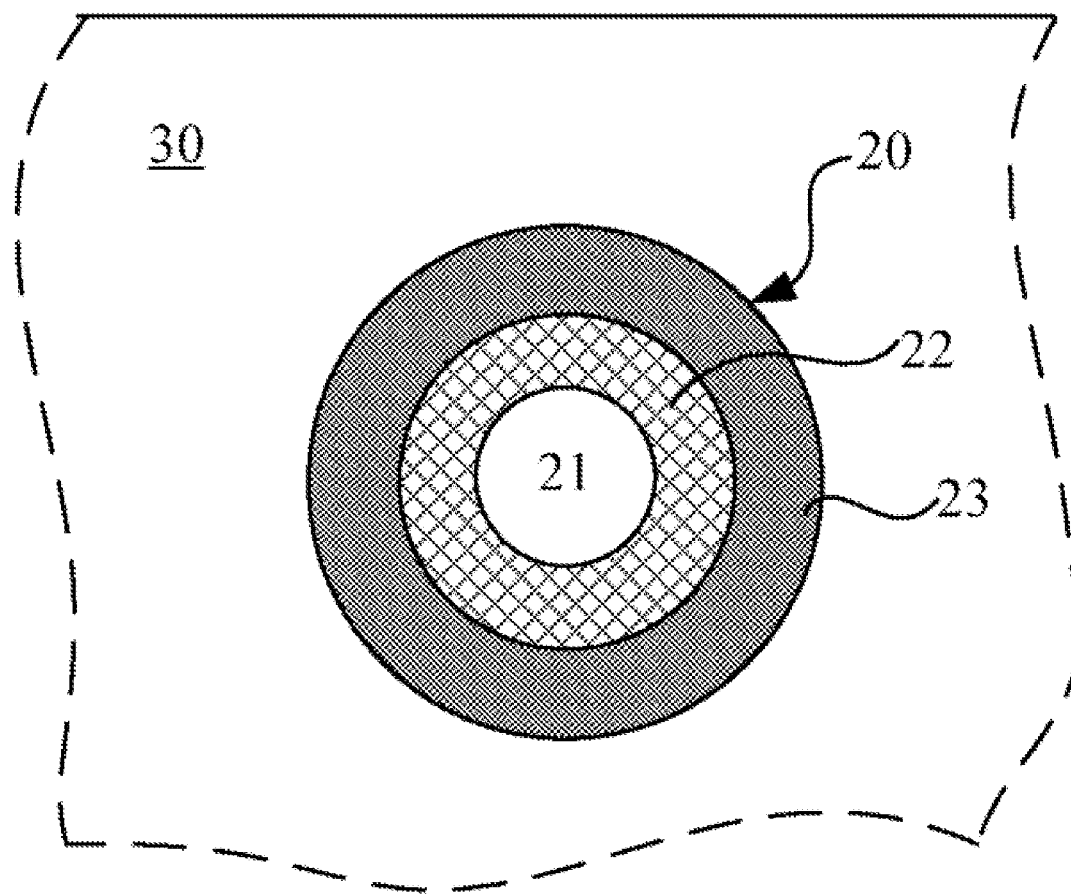
FIG. 5 is a schematic section diagram showing a core-shell structure of the polylactic acid composite material according to the second embodiment of the present invention.

FIG. 5 is a schematic sectional diagram showing a core-shell structure of the polylactic acid composite material according to the second embodiment of the present invention.

As shown in FIG. 5, in the present embodiment, the core-shell structure 20 can comprise a substrate particle 21, an intermediate layer 22, and a polymer layer 23. Specifically, in the core-shell structure 20, the outer surfaces of the substrate particle 21 are covered with the intermediate layer 22, and the polymer layer 23 is formed on the outer surface of the intermediate layer 22. In some examples, the core-shell structure 20 can be uniformly dispersed in the polylactic acid matrix 30. In this case, the surface-modified substrate particle 21 is provided, and the core-shell structure 20 is added to the polylactic acid matrix 30, such that the interfacial interaction force between the substrate particle 21 and the polylactic acid matrix 30 can be enhanced, the dispersion of the substrate particle 21 in the polylactic acid matrix 30 can be improved, and meanwhile, the mechanical strength and toughness of the polylactic acid composite material 2 are improved.

In the present embodiment, the substrate particle 21, the intermediate layer 22, and the polymer layer 23 in the core-shell structure 20 can correspond to the substrate particle 11, the intermediate layer 12, and the polymer matrix 13 of the first embodiment, respectively, and can, for example, be made of the same constituent material as those in the first embodiment.

Substrate Particle

In the present embodiment, the substrate particle 21 can contain a calcium phosphate compound. Preferably, the substrate particle 21 can contain one or more selected from the group consisting of hydroxyapatite, calcium polyphosphate, and tricalcium phosphate. In this case, the bioactivity of the polylactic acid composite material 2 is improved and the repairing effect thereof on human bone tissues is promoted.

It is well known that among inorganic constituents of human bone tissues, calcium phosphate compounds are dominant. After the polylactic acid composite material 2 according to the present embodiment being implanted into human body as an orthopedic repair material, the intermediate layer 22 and the polymer layer 23 (described later) will be absorbed by the human body, and therefore, elements such as calcium and phosphorus contained in the substrate particle 21 are absorbed by body tissues to form new bone tissues, thereby contributing to bone growth and repair.

Further, the substrate particle 21 is not limited to the above-described hydroxyapatite, calcium polyphosphate, tricalcium phosphate or the like. In the present embodiment, the substrate particle 21 can improve the repairing effect of the polylactic acid composite material 2 on human bone tissues as long as the substrate particle 21 contain substances similar to the constituents of the human bone tissues.

Further, in the present embodiment, preferably, the substrate particle 21 is rigid particle. In some examples, the substrate particle 21 can be rigid particles having a Young's modulus greater than $2\times10^{11}$ Pa. In this case, the mechanical strength of the polylactic acid composite material 1 can be effectively improved.

Further, in the present embodiment, the shape of the substrate particle 21 is not particularly limited. For example, in some examples, the substrate particle 21 can be spherical. However, the present embodiment is not limited thereto, and in other examples, the substrate particle 21 can be ellipsoidal, irregularly stereoscopic, or the like.

In the present embodiment, the mass percentage (wt %) of the substrate particle 21 is not particularly limited. In view of the mechanical strength and toughness of the polylactic acid composite material 2, the mass percentage of the substrate particle 21 is preferably from 1 wt % to 30 wt %, for example, the mass percentage of the substrate particle 21 can be 1 wt %, 3 wt %, 5 wt %, 8 wt % or 15 wt %, 20 wt %, 25 wt % or 30 wt %. Specifically, in the polylactic acid composite material 2, the substrate particle 21 function as improving the mechanical strength of the polylactic acid composite material, and generally, the more the content of the substrate particle 21, the higher the mechanical strength of the polylactic acid composite material 2; when the content of the substrate particle 21 is relatively low, the mechanical strength of the polylactic acid composite material 2 is insufficient, and when the content of the substrate particle 21 is excessive, the toughness and other performance features of the polylactic acid composite material 2 will be affected. Therefore, by taking the mass percentage of the substrate particle 21 at 1 wt % to 30 wt %, the mechanical strength of the polylactic acid composite material 2 can be improved, and the toughness and other performance features of the polylactic acid composite material 2 can be prevented from being affected or less affected.

In the present embodiment, an average particle diameter of the substrate particle 21 is not particularly limited. In view of the mechanical strength and toughness of the polylactic acid composite material 2, the average particle diameter of the substrate particle 21 is preferably from 5 nm to 200 μm, for example, the average particle diameter of the substrate particle 21 can be 5 nm, 10 nm, 30 nm, 50 nm, 1 μm, 2 μm, 5 μm, 10 μm, 20 μm, 30 μm, 50 μm, 80 μm, 100 μm, 130 μm, 150 μm, 180 μm or 200 μm. Specifically, the smaller the particle diameter of the substrate particle 21 generally is, the stronger the rigidity thereof is. Therefore, when the substrate particle 21 having relatively small particle diameter is selected, the effect of the substrate particle 21 on the increase of the mechanical strength of the polylactic acid composite material 2 can be sufficiently exerted; as the particle size of the substrate particle 21 increases, the surface energy thereof is reduced, and agglomeration can be suppressed to some extent, but when the particle size of the substrate particle 21 is too large, the uniformity of dispersion thereof will be affected, thereby affecting the mechanical strength of the polylactic acid composite material 2. Therefore, by limiting the particle diameter of the substrate particle 21 within the above range, the mechanical strength of the polylactic acid composite material 2 can be enhanced, and the dispersion of the substrate particle 21 is kept uniform enough.

Intermediate Layer

In the present embodiment, the intermediate layer 22 can be coated on the surfaces of the substrate particle 21. That is, the intermediate layer 22 covers the surfaces of the substrate particle 21. Additionally, the intermediate layer 22 can have a fourth glass transition temperature T4. In some examples, the fourth glass transition temperature T4 cannot be higher than a normal human body temperature. In general, for a glass transition temperature of a substance, when the external temperature is higher than a glass transition temperature of a polymer, the substance will be in an elastic state or a rubbery state; and when the external temperature is lower than or equal to the glass transition temperature of the polymer, the substance will be in a glassy state.

When the polylactic acid composite material 2 according to the present embodiment is applied to a human body, since the first glass transition temperature T4 of the intermediate layer 22 is not higher than the normal human body temperature (for example, 37° C.), the intermediate layer 22 can be maintained in a rubbery state. In this case, the intermediate layer 22 in the rubbery state can release (for example, release in situ) the stress concentration caused by the substrate particle 21 and alleviate the resulting microcracks, whereby the toughness of the polylactic acid composite material 2 can be improved. In addition, the substrate particle 21 can also suppress (for example, suppress in situ) the severe deformation of the intermediate layer 22 in the rubbery state under a certain stress, whereby the decrease in the mechanical strength of the polylactic acid composite material 2 can be suppressed.

In the present embodiment, the intermediate layer 22 can contain a homopolymer of a monomer selected from one of p-dioxanone and caprolactone. Moreover, the intermediate layer 22 can also be a binary or higher order random copolymer or block copolymer selected from the group consisting of lactide, caprolactone, p-dioxanone, and glycolide. In this case, the intermediate layer 22 can form an absorbable polymer material, which facilitates the application of the polylactic acid composite material 2 in the field of orthopedics, especially in the field of absorbable orthopedic materials.

As described above, in the present embodiment, the fourth glass transition temperature T4 of the intermediate layer 22 can be not higher than the normal human body temperature. In addition, the specific numerical range of the fourth glass transition temperature T4 is not particularly limited. Preferably, the fourth glass transition temperature T4 satisfies $-37°$ C.$\leq$T4$\leq$36° C., and more preferably, $-10°$ C.$\leq$T4$\leq$36° C.

In addition, in the present embodiment, the magnitude of the glass transition temperature T4 of the intermediate layer 22 can be adjusted according to actual needs. For a homopolymer, different glass transition temperatures T4 can be obtained by adjusting the variety or mass of monomers thereof; for a copolymer, the glass transition temperature T4 can be changed by adjusting proportions of monomers thereof in mixed monomers.

In the present embodiment, the intermediate layer 22 can be composed of a polymer material. In this case, the substrate particle 21 can be bonded to the intermediate layer 22 via covalent bonds, such that a strong interfacial interaction force is formed between the substrate particle 21 and the intermediate layer 22, thereby effectively improving the bonding force therebetween, thereby facilitating the force transmission. In addition, the substrate particle 21 can be bonded to the intermediate layer 22 by a strong interfacial interaction force such as ionic bonds.

In the clinical application of human orthopedics repair, when a strong force exists between the intermediate layer 22 in the rubbery state and the substrate particle 21, it can contribute to the force transmission between the intermediate layer 22 and the substrate particle 21 and promote a linkage effect therebetween. To be specific, on the one hand, the intermediate layer 22 in the rubbery state can release (for example, release in situ) the stress concentration caused by the substrate particle 21 and alleviate the resulting microcracks, whereby the toughness of the polylactic acid composite material 2 can be improved; and on the other hand, the substrate particle 21 can also suppress (for example, suppress in situ) the severe deformation of the intermediate layer 22 in the rubbery state under a certain stress, whereby the decrease in the mechanical strength of the polylactic acid composite material 2 caused by the addition of the intermediate layer 22 in the rubbery state can be suppressed. Therefore, the strength and toughness of the polylactic acid composite material 2 can be simultaneously improved, which is of important significance in the application of the polylactic acid composite material 2 according to the present embodiment in orthopedic medical appliances.

Further, in the present embodiment, a molding method of the intermediate layer 22 is not particularly limited. In some examples, the intermediate layer can be formed by initiating in-situ polymerization on the outer surfaces of the substrate particle 21. Further, in other examples, the intermediate layer can also be formed by modifying the surfaces of the substrate particle 21.

Polymer Layer

In the present embodiment, the polymer layer 23 is formed on the outer surface of the intermediate layer 22. A stereocomplex can be formed between the polymer layer 23 and the polylactic acid matrix 30 (described later). In general, the stereocomplex functions as special hydrogen bonds, that is, a stereocomplex function, which are more stable than common hydrogen bonds, and thus the resulting stereocomplex also has a higher melting point and more excellent mechanical properties.

In the present embodiment, in the stereocomplex formed between the polymer layer 23 and the polylactic acid matrix 30, the stereocomplex force between the polymer layer 23 and the polylactic acid matrix 30 contributes to the force transmission between the polylactic acid matrix 30 and the intermediate layer 22 in the rubbery state and is thus capable of improving the mechanical strength of the polylactic acid composite material 2. In addition, the stereocomplex force can also increase the dispersion of the core-shell structure 20 in the polylactic acid matrix 30, thereby improving the mechanical strength and toughness of the polylactic acid composite material 2 simultaneously.

In addition, in the present embodiment, a molding method of the polymer layer 23 is not particularly limited. Preferably, the polymer layer can be formed by initiating in-situ polymerization on the outer surface of the intermediate layer 22.

In the present embodiment, the polymer layer 23 can contain a homopolymer of a first type of lactide monomer. Moreover, the polymer layer 23 can also contain a random copolymer or block copolymer of a first type of lactide and one or more monomers selected from the group consisting of a second type of lactide, caprolactone, p-dioxanone, and glycolide. Therefore, the polymer layer 23 can form poly (L-lactic acid) or poly(D-lactic acid), or a copolymer having poly(L-lactic acid) or poly(D-lactic acid), so as to form a stereocomplex with the polylactic acid matrix 30 to produce a stereocomplex effect.

Further, in the present embodiment, the molecular weight of the polymer layer 23 is not particularly limited, for example, the polymer layer 23 can have a relatively small molecular weight to form a short-chain polymer layer 23, or the polymer layer 23 can have a relatively large molecular weight to form a long-chain polymer layer 23.

In addition, in the present embodiment, the glass transition temperature of the polymer layer 23 is not particularly limited. Alternatively, the glass transition temperature of the polymer layer 23 can be the same as the glass transition temperature of the intermediate layer 22, or can be higher or lower than the glass transition temperature of the intermediate layer 22.

Polylactic Acid Matrix

In the present embodiment, the polylactic acid matrix 30 can form a stereocomplex with the polymer layer 23 of the core-shell structure 20. As described above, the stereocomplex functions as special hydrogen bonds, that is, a stereocomplex function, which are more stable than common hydrogen bonds, and thus has a higher melting point and more excellent mechanical properties. In addition, the stereocomplex force of the stereocomplex contributes to the force transmission between the polylactic acid matrix 30 and the intermediate layer 22 in the rubbery state and is thus capable of increasing the dispersion of the core-shell structure 20 in the polylactic acid matrix 30, thereby improving the mechanical strength and toughness of the polylactic acid composite material 2 simultaneously.

In the present embodiment, the polylactic acid matrix 30 can include a plurality of core-shell structures 20, and the plurality of core-shell structures 20 can be dispersed in the polylactic acid matrix 30. In addition, the size of the plurality of core-shell structures 20 is not particularly limited, in some examples, the plurality of core-shell structures 20 can be uniform in size, and in other examples, the plurality of core-shell structures 20 can be different in size.

In the present embodiment, the polylactic acid matrix 30 can have a third glass transition temperature T3. In addition, the third glass transition temperature T3 can be higher than the fourth glass transition temperature T4 of the intermediate layer 22 of the core-shell structure 20, that is, T3>T4. Thus, under the same temperature conditions, the polylactic acid matrix 30 can maintain better mechanical strength than the core-shell structure 20, thereby enhancing the mechanical properties of the polylactic acid composite material 2.

Further, in the present embodiment, the third glass transition temperature T3 of the polylactic acid matrix 30 can be higher than the normal body temperature. Therefore, when the polylactic acid composite material 2 according to the present embodiment is applied to a human body, it can be kept in a glassy state, such that the mechanical strength of the polylactic acid composite material 2 can be further ensured to be high enough.

In the present embodiment, the polylactic acid matrix 30 can contain a homopolymer of a second type of lactide monomer. Moreover, the polylactic acid matrix 30 can also contain a random copolymer or block copolymer of a second type of lactide and one or more monomers selected from the group consisting of a first type of lactide, caprolactone, p-dioxanone, and glycolide. In some examples, the first type of lactide and the second type of lactide can be levoisomer-dextroisomer of lactide for each other.

In this case, the polylactic acid matrix 30 and the polymer layer 23 of the core-shell structure 20 can form levoisomer and dextroisomer of the polylactic acid respectively. The polylactic acid matrix 30 can generate special hydrogen bonds, that is, a stereocomplex force, which are more stable than common hydrogen bonds, thereby forming a stereocomplex when it is in contact with the polymer layer 23 of the core-shell structure 20. Since the stereocomplex has a higher melting point and better mechanical properties than poly(L-lactic acid) or poly(D-lactic acid) alone, the mechanical properties of the polylactic acid composite material 2 can be further improved.

As described above, in the present embodiment, the polymer layer 23 of the core-shell structure 20 can form a stereocomplex with the polylactic acid matrix 30. In the stereocomplex, the stereocomplex crystallization ratio is not particularly limited, and in some examples, in view of the mechanical properties, the stereocomplex crystallization ratio is preferably from 1% to 40%, for example, the stereocomplex crystallization ratio can be 1%, 5%, 10%, 20%, 30% or 40%. In general, the larger the stereocomplex crystallization ratio is, the more stereocomplexes formed in the composite material, and the stronger the corresponding stereocomplex force will be, that is, the stronger the mechanical properties of the composite material will be.

Figure 6:
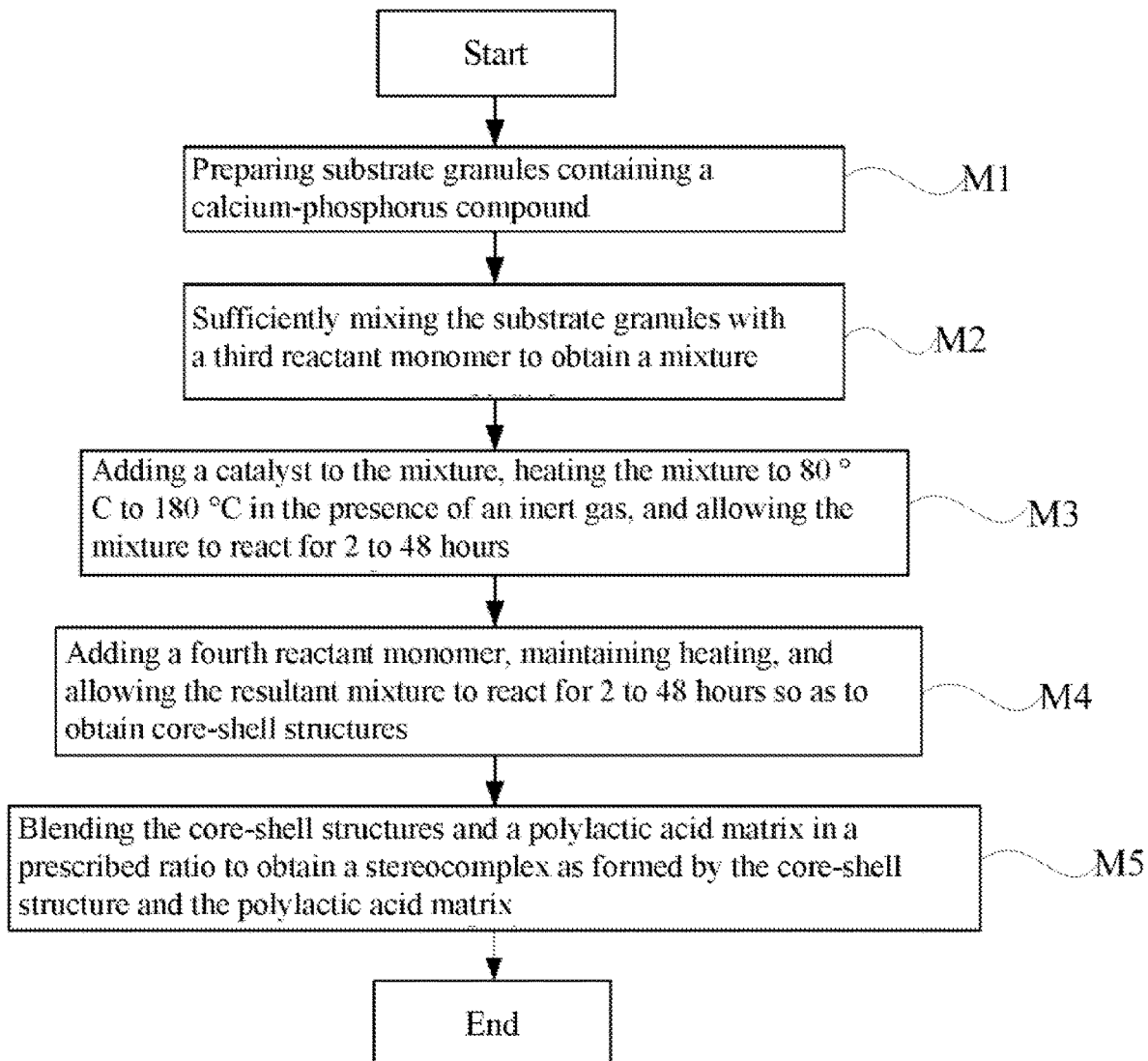
FIG. 6 is a schematic diagram showing the preparation steps of the absorbable biomedical polylactic acid composite material according to the second embodiment of the present invention.

FIG. 6 is a schematic diagram showing a preparation method of an absorbable biomedical polylactic acid composite material.

Hereinafter, a preparation method for the absorbable biomedical polylactic acid composite material according to the present embodiment will be described in detail with reference to FIG. 6.

As shown in FIG. 6, the preparation method for the absorbable biomedical polylactic acid composite material according to the present embodiment can comprise the following steps: preparing a substrate particle 21 containing a calcium phosphate compound (step M1); sufficiently mixing the substrate particle 21 with a third reactive monomer to obtain a mixed solution (step M2); adding a catalyst to the mixed solution, and heating to 80° C. to 180° C. in the presence of inert gas, and reacting for 2 hours to 48 hours, such that an intermediate layer 22 composed of the third reactive monomer is coated on the substrate particle 21 (step M3); adding a fourth reactive monomer, maintaining heating, and continuing to react for 2 hours to 48 hours to form a polymer layer 23 on the intermediate layer, thereby obtaining a core-shell structure 20 (step M4); and blending the core-shell structure 20 and the polylactic acid matrix 30 in a preset ratio to obtain a stereocomplex formed by the core-shell structure 20 and the polylactic acid matrix 30, thereby obtaining a polylactic acid composite material 2 (step M5).

In the present embodiment, in step M1, the substrate particle 21 containing the calcium phosphate compound are first prepared. In some examples, the substrate particle 21 can be selected from one or more of hydroxyapatite, calcium polyphosphate, and tricalcium phosphate. It is well known that among inorganic constituents of human bone tissues, calcium phosphate compounds are dominant. After the polylactic acid composite material 2 according to the present embodiment is implanted into the body as an orthopedic repair material, the intermediate layer 22 and the polymer matrix 23 (described later) will be absorbed by the human body, and therefore, elements such as calcium and phosphorus contained in the substrate particle 21 are absorbed by body tissues to form new bone tissues, thereby contributing to bone growth and repair.

Further, the substrate particle 21 is not limited to the above-described hydroxyapatite, calcium polyphosphate, tricalcium phosphate or the like. In the present embodiment, the substrate particle 21 can also improve the repairing effect of the polylactic acid composite material 2 on the human bone tissues as long as the substrate particle 21 contains substances similar to the constituents of the human bone tissues.

In the present embodiment, in step M2, the substrate particle 21 in the step M1 can be sufficiently mixed with the third reactive monomer to obtain the mixed solution. In some examples, in step M2, the substrate particle 21 can be first dissolved in an organic solvent, and then the first reactive monomer is added and sufficiently mixed to form a mixed organic solution.

In the present embodiment, in step M3, the catalyst is added to the mixed solution obtained in the step M2, and heated to 80° C. to 180° C. in the presence of inert gas, and the reaction is performed for 2 hours to 48 hours to obtain the intermediate layer 22 coated on the surfaces of the matrix particles 21.

Therein, the third reactive monomer can be selected one from the group consisting of lactide, caprolactone, p-dioxanone, and glycolide. Further, the third reactive monomer can be selected two or more from the group consisting of lactide, caprolactone, p-dioxanone, and glycolide. In this case, the resulting intermediate layer 22 is a homopolymer containing a monomer selected from p-dioxanone or caprolactone, or is a binary or higher order random copolymer or block copolymer selected from the group consisting of lactide, caprolactone, p-dioxanone, and glycolide. Thus, the intermediate layer 22 can form an absorbable polymeric material that facilitates the application of the polylactic acid composite material 2 in the field of orthopedics, particularly in the field of absorbable orthopedic materials.

In the present embodiment, the intermediate layer 22 can be composed of a polymer material, and the substrate particle 21 can be bonded to the intermediate layer 22 via covalent bonds. In the clinical application of human orthopedics repair, when there is a strong force between the intermediate layer 22 in the rubbery state and the substrate particle 21, it can contribute to the force transmission between the intermediate layer 22 and the substrate particle 21 and promote a linkage effect therebetween. To be specific, on the one hand, the intermediate layer 22 in the rubbery state can release in situ and alleviate the stress concentration and microcracks caused by the substrate particle 21, whereby the toughness of the polylactic acid composite material 2 can be improved; and on the other hand, the substrate particle 21 can also suppress in situ the severe deformation of the intermediate layer 22 in the rubbery state under a certain stress, whereby the decrease in the mechanical strength of the polylactic acid composite material 2 caused by the addition of the intermediate layer 22 in the rubbery state can be effectively avoided. In summary, the excellent force transmission and linkage effect can be achieved by the bonding of the intermediate layer 22 and the substrate particle 21 via covalent bonds, such that the mechanical strength and toughness of the polylactic acid composite material 2 can be simultaneously improved, which is of important significance in the application of orthopedic medical appliances.

Further, in step M3, the catalyst is preferably stannous octoate. Therefore, in-situ polymerization of monomers can be initiated to form a strong interfacial interaction force such as covalent bonds.

Further, in the present embodiment, the inert gas can be nitrogen gas or argon gas. Therefore, the successful occurrence of the reaction can be ensured, and the formation of other impurities can be effectively avoided.

In the present embodiment, in step M4, in the reaction system of step M3, the fourth reactive monomer is added, heating is maintained, and the reaction is continued for 2 hours to 48 hours, thereby forming a polymer layer 23 on the intermediate layer 22 and finally obtaining the core-shell structure 20.

Therein, the third reactive monomer can be a first type of lactide, or a first type of lactide and one or more selected from the group consisting of a second type of lactide, caprolactone, p-dioxanone, and glycolide. In this case, the resulting polymer layer 23 is a homopolymer containing the first type of lactide monomer, or a random copolymer or block copolymer of the first type of lactide and one or more monomers selected from the group consisting of the second type of lactide, caprolactone, p-dioxanone, and glycolide.

Further, in the present embodiment, the products of the two stages of the step M3 and the step M4 are dissolved in an organic solvent respectively. Preferably, the organic solvent is chloroform. Next, free molecular chains which are not grafted to the substrate particle 21 are separated and removed by centrifugation to obtain a composition of the matrix particles 21 and the intermediate layer 22 (substrate particle 21-intermediate layer 22), and a core-shell structure 20, respectively. Therein, the removed free molecular chains, that is, the intermediate layer 22 and the composition of the intermediate layer 22 and the polymer layer 23 (intermediate layer 22-polymer layer 23), were subjected to DSC testing to detect the glass transition temperature of the material.

In the present embodiment, in step M5, the core-shell structure 20 prepared in the step M4 and the polylactic acid matrix 30 are blended in a preset ratio to obtain a stereocomplex formed by the core-shell structure 20 and the polylactic acid matrix 30, and therefore the polylactic acid composite material 2 is obtained.

Therein, the polylactic acid matrix 30 can contain a homopolymer of a second type of lactide monomer. Moreover, the polylactic acid matrix 30 can also contain a random copolymer or block copolymer of a second type of lactide and one or more monomers selected from the group consisting of a first type of lactide, caprolactone, p-dioxanone, and glycolide, and the first type of lactide and the second type of lactide can be levoisomer-dextroisomer of lactide for each other. In this case, the polymer layer 23 and the polylactic acid matrix 30 can form levoisomer and dextroisomer of the polylactic acid respectively. Special hydrogen bonds which are more stable than common hydrogen bonds can be generated, thereby forming a stereocomplex when the polylactic acid matrix 30 is in contact with the polylactic acid matrix 30. Since the stereocomplex has a higher melting point and better mechanical properties than poly(L-lactic acid) or poly(D-lactic acid) alone, the mechanical properties of the polylactic acid composite material can be further improved.

Therefore, the core-shell structure 20 containing the polymer layer 23 forms a stereocomplex force with the polylactic acid matrix 30, which contributes to the force transmission between the polylactic acid matrix 30 and the intermediate layer 22 of the core-shell structure 20 and is capable of assisting in the dispersion of the substrate particle 21 of the core-shell structure 20 in the polylactic acid matrix 30. This material structure design can bring excellent force transmission and linkage effect on the polylactic acid composite material 2, such that the mechanical strength and toughness of the polylactic acid composite material 2 can be improved, which is of great significance in the application of orthopedic medical appliances.

Further, as described above, in step M5, the organic solvent (the first organic solvent) in which the core-shell structure 20 and the polylactic acid matrix 30 are blended can be chloroform. Further, in step S5, the organic solvent (the second organic solvent) in which the reacted system is precipitated to obtain the polylactic acid composite material 2 can be methanol. Further, in the present embodiment, the first organic solvent is different from the second organic solvent.

Further, in the present embodiment, the polylactic acid composite material 2 obtained in the step M5 is subjected to injection molding, and the mechanical property analysis results are obtained by testing.

In the present embodiment, the absorbable biomedical polylactic acid composite material 2 prepared by the step M1 to the step M5 comprises the core-shell structure 20 and the polylactic acid matrix 30 that forms a stereocomplex force with the core-shell structure 20. This stereocomplex force not only contributes to the force transmission between the polylactic acid matrix 30 and the core-shell structure 20, but also can contribute to the dispersion of the core-shell structure 20 in the polylactic acid matrix 30.

Further, in the core-shell structure 20, the intermediate layer 22 is further provided between the substrate particle 21 and the polymer layer 23. As described above, the glass transition temperature of the intermediate layer 22 is not higher than the normal human body temperature, and therefore, when the polylactic acid composite material 2 according to the present embodiment is applied to orthopedic clinical treatment, the intermediate layer 22 of the core-shell structure 20 can be maintained in a rubbery state in the human body, and the intermediate layer 22 in the rubbery state can release the stress concentration and microcracks caused by the substrate particle 21, whereby the toughness of the polylactic acid composite material 2 can be improved. Meanwhile, the substrate particle 21 can also suppress the severe deformation of the intermediate layer 22 in the rubbery state under a certain stress, whereby the decrease in the mechanical strength of the polylactic acid composite material 2 can also be suppressed.

In order to further describe the present invention, the absorbable biomedical polylactic acid composite material and the preparation method therefor provided by the present invention are described in detail below with reference to the examples, and the beneficial effects achieved by the present invention are fully described in conjunction with the comparative examples.

EXAMPLE 4

2 g of hydroxyapatite having a particle diameter of 5 nm was dispersed in 100 ml of toluene; 9 g of caprolactone monomer, 6 g of L-lactide monomer and 160 ul of stannous octoate were then added and heated with stirring to 80° C. in the presence of inert gas, and the reaction was performed for 2 hours. Then, 5 g of D-lactide was added and the reaction was continued for 2 hours.

The products obtained in the two stages were dissolved with chloroform respectively, and free molecular chains which were not grafted to the hydroxyapatite were separated and removed by centrifugation to obtain a hydroxyapatite and a rubbery layer polymer (hydroxyapatite-rubbery layer) and a core-shell structure constituted by hydroxyapatite and a rubbery layer and poly(D-lactic acid), respectively. The removed free molecular chains, that is, the rubbery molecular chain and the rubbery layer-poly(D-lactic acid) polymer molecular chain were subjected to DSC testing to detect the glass transition temperature of the material. The results are shown in Table 3.

TABLE 3

| Sample | | Glass transition temperature (Tg, ° C.) |
|---|---|---|
| Example 4 | Rubbery layer | −35 |
| | Rubbery layer-poly(D-lactic acid) | −16 |
| Example 5 | Rubbery layer | −10 |
| | Rubbery layer-poly(D-lactic acid) caprolactone random copolymer | 40 |
| Example 6 | Rubbery layer | −37 |
| | Rubbery layer-poly(D-lactic acid) glycolide block copolymer | 17 |
| Comparative Example 4 | Rubbery layer | −35 |
| | Rubbery layer-poly(L-lactic acid) | −17 |
| Comparative Example 5 | Poly(D-lactic acid) | 55 |

Finally, the core-shell structure and the poly(L-lactic acid) (Mn=120,000, glass transition temperature of 55° C.) were blended in chloroform, and precipitated in methanol to obtain a polylactic acid composite material. The composite material was subjected to mechanical testing after injection molding, and the results are shown in Table 4.

For the polylactic acid composite material, the mass percentage of the hydroxyapatite is 1% under TGA testing, and the stereocomplex crystallization ratio of the polylactic acid composite material is 1% under DSC testing.

TABLE 4

| Sample | Young's modulus (GPa) | Tensile strength (MPa) | Elongation at break (%) |
|---|---|---|---|
| Example 4 | 3.8 | 44.1 | 12.9 |
| Example 5 | 4.6 | 52.2 | 26.1 |
| Example 6 | 4.5 | 50.1 | 21.2 |
| Comparative Example 4 | 3.4 | 42.2 | 8.4 |
| Comparative Example 5 | 4.0 | 46.2 | 2.4 |
| Comparative example 6 | 3.2 | 38.2 | 4.2 |

EXAMPLE 5

2 g of calcium polyphosphate having a particle diameter of 200 um was dispersed in 8 g of p-dioxanone monomer; 160 μl of stannous octoate was then added and heated with stirring to 180° C. in the presence of inert gas, and the reaction was performed for 48 hours. Then, 5 g of D-lactide and 1 g of caprolactone were added and the reaction was continued for 48 hours.

The products obtained in the two stages were dissolved with chloroform respectively, and free molecular chains which were not grafted to the calcium polyphosphate were separated and removed by centrifugation to obtain a calcium polyphosphate and a rubbery layer polymer (calcium polyphosphate-rubbery layer), and a core-shell structure constituted by hydroxyapatite and a rubbery layer and poly(D-lactic acid) caprolactone random copolymer, respectively. The removed free molecular chains, that is, the rubbery molecular chain and the rubbery layer and poly(D-lactic acid) caprolactone random copolymer molecular chain were subjected to DSC testing to detect the glass transition temperature of the material. The results are shown in Table 3.

The polylactic acid matrix material was obtained by the following method: 25 mg of ethylene glycol, 160 μl of stannous octoate, 45 g of L-lactide and 5 g of caprolactone were heated with stirring to 180° C., reacted for 48 hours, and then purified by a chloroform-methanol system, wherein the obtained polylactic acid matrix material is a poly(L-lactic acid) caprolactone random copolymer (Mn=110,000, glass transition temperature of 50° C.).

The core-shell structure and the polylactic acid matrix material were blended in chloroform and precipitated in methanol to obtain a polylactic acid composite material. The composite material was subjected to mechanical testing after injection molding, and the results are shown in Table 4.

For the polylactic acid composite material, the mass percentage of the hydroxyapatite is 30% under TGA testing, and the stereocomplex crystallization ratio of the polylactic acid composite material is 40% under DSC testing.

EXAMPLE 6

2 g of tricalcium phosphate having a particle diameter of 200 nm was dispersed in 100 ml of toluene; then 6 g of caprolactone monomer and 160 μl of stannous octoate were added, and heated with stirring to 150° C. in the presence of inert gas, and the reaction was performed for 12 hours; 6 g of glycolide monomer was then added, and the reaction was performed for 12 hours; then 3 g of caprolactone monomer was added and the reaction was performed for 6 hours, thereby obtaining a tricalcium phosphate and a rubbery layer polymer (tricalcium phosphate-rubbery layer).

Then, 5 g of D-lactide was added to the reaction system, and the reaction was performed for 3 hours; then 2 g of glycolide was added, and the reaction was performed for 2 hours; and then 3 g of D-lactide was added, and the reaction was performed for 4 hours, to obtain a core-shell structure constituted by tricalcium phosphate and a rubbery layer and poly(D-lactic acid) glycolide block copolymer.

The products obtained in the two stages were dissolved with chloroform respectively, and free molecular chains which were not grafted to the tricalcium phosphate were separated and removed by centrifugation to obtain a tricalcium phosphate and rubbery layer polymer (tricalcium phosphate-rubbery layer) and a core-shell structure, respectively. The removed free molecular chains, that is, the rubbery molecular chain and the polymer molecular chain of the rubbery layer and poly(D-polylactic acid) lactide block copolymer (rubbery layer-poly(D-lactic acid) glycolide block copolymer) were subjected to DSC testing to detect the glass transition temperature of the material. The results are shown in Table 3.

The polylactic acid matrix material is obtained by the following method: 25 mg of ethylene glycol, 160 μl of stannous octoate, and 45 g of L-lactide were heated with stirring to 180° C., and the reaction is performed for 36 hours; then, 5 g of caprolactone is added, and the reaction is continued for 12 hours and purified by a chloroform-methanol system, wherein the obtained polylactic acid matrix material is a poly(L-lactic acid) caprolactone block copolymer (number-average molecular weight Mn=105,000, glass transition temperature of 50° C.).

The core-shell structure and the polylactic acid matrix material were finally blended in chloroform and precipitated in methanol to obtain a polylactic acid composite material. The composite material was subjected to mechanical testing after injection molding, and the results are shown in Table 4.

For the polylactic acid composite material, the mass percentage of the hydroxyapatite is 15% under TGA testing, and the stereocomplex crystallization ratio of the polylactic acid composite material is 20% under DSC testing.

Comparative Example 4

2 g of hydroxyapatite having a particle diameter of 5 nm was dispersed in 100 ml of toluene, then 9 g of caprolactone monomer, 6 g of L-lactide monomer and 160 μl of stannous octoate were added and heated with stirring to 80° C. in the presence of inert gas, and the reaction was performed for 2 hours. Then, 5 g of L-lactide was added and the reaction was continued for 2 hours.

The products obtained in the two stages were dissolved with chloroform respectively, and free molecular chains which were not grafted to the hydroxyapatite were separated and removed by centrifugation to obtain a hydroxyapatite and a rubbery layer polymer (hydroxyapatite-rubbery layer), and a core-shell structure constituted by hydroxyapatite and a rubbery layer and poly(L-lactic acid), respectively. The removed free molecular chains, that is, the rubbery molecular chain and the rubber layer and the poly(D-lactic acid) polymer molecular chain were subjected to DSC testing to detect the glass transition temperature of the material. The results are shown in Table 3.

The core-shell structure and the poly(L-lactic acid) (Mn=120,000, glass transition temperature of 55° C.) were finally blended in chloroform and precipitated in methanol to obtain a polylactic acid composite material. The composite material was subjected to mechanical testing after injection molding, and the results are shown in Table 4.

The mass percentage of the hydroxyapatite in the polylactic acid composite material is 1% under TGA testing.

Comparative Example 5

2 g of hydroxyapatite having a particle diameter of 5 nm was dispersed in 100 ml of toluene, 5 g of D-lactide and 160 μl of stannous octoate were then added and heated with stirring to 80° C. in the presence of inert gas, and the reaction was performed for 2 hours.

The product obtained in the above step was dissolved with chloroform, and free molecular chains which were not grafted to the hydroxyapatite were separated and removed by centrifugation to obtain a hydroxyapatite and poly(D-lactic acid) polymer (hydroxyapatite-poly(D-lactic acid)). The removed free molecular chains, that is, the poly(D-lactic acid) molecular chains were subjected to DSC (Differential Scanning calorimetry) testing to detect the glass transition temperature of the material. The results are shown in Table 1.

The hydroxyapatite and poly(D-lactic acid) polymer (hydroxyapatite-poly(D-lactic acid) and the poly(L-lactic acid) (Mn=120,000, glass transition temperature of 55° C.) were finally blended in chloroform and precipitated in methanol to obtain a polylactic acid composite material. The composite material was subjected to mechanical testing after injection molding, and the results are shown in Table 2.

The mass percentage of the hydroxyapatite in the polylactic acid composite material is 1% under TGA (Thermogravimetric Analysis) testing.

Comparative Example 6

The poly(L-lactic acid) (Mn=120,000, glass transition temperature of 55° C.) was subjected to injection molding, and the tensile mechanical property test results is shown in Table 4.

As shown in Table 3 and Table 4, it can be seen from the comparison of Example 4 and Comparative Example 6 that the interface design method of the present invention can simultaneously effectively improve the mechanical strength (represented by Young's modulus and tensile strength) and the toughness (represented by elongation at break) of the polylactic acid composite material.

As can be seen from the comparison of Example 4 and Comparative Example 5, the cushion effect of the rubbery layer formed between the substrate particle and the polylactic acid matrix material is helpful for improving the toughness of the polylactic acid composite material.

In Comparative Example 4, there is no strong stereocomplex interfacial interaction force between the core-shell structure and the polylactic acid matrix, so it can be seen from the comparison of Example 4 and Comparative Example 4 that the stereocomplex force in the absorbable polylactic acid composite material of the present invention plays an important role in improving the mechanical properties of the material.

Although the present invention has been described in detail with reference to the accompanying drawings and embodiments, it can be understood that the above description is not intended to limit the present invention in any way. The present invention can be modified and changed as needed by the skilled in the art without departing from the spirit and scope of the present invention, and these modifications and variations fall within the scope of the present invention.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:
1. An absorbable biomedical polylactic acid composite material, comprising:
   a core-shell structure comprising a substrate particle containing calcium phosphate, an intermediate layer coated on the substrate particle, and a polymer layer formed on an outer surface of the intermediate layer; and a polylactic acid matrix which forms a stereocomplex with the polymer layer of the core-shell structure and has a third glass transition temperature;
wherein:
the polylactic acid composite material comprises 1 wt % to 10 wt % of the intermediate layer; the substrate particle and the intermediate layer are bonded via covalent bonds; the intermediate layer comprises a homopolymer of a monomer selected from the group consisting of p-dioxane and caprolactone; a binary or higher order random copolymer selected from the group consisting of lactide, caprolactone, p-dioxane, and glycolide; or a block copolymer selected from the group consisting of lactide, caprolactone, p-dioxanone, and glycolide; the polymer layer comprises poly(L-lactic acid), poly(D-lactic acid), a copolymer having poly(L-lactic acid), or a copolymer having poly(D-lactic acid);
the intermediate layer and the polymer layer do not form a stereocomplex;
the substrate particle and the intermediate layer do not form a stereocomplex;
the intermediate layer has a fourth glass transition temperature which is not higher than normal human body temperature; and
the third glass transition temperature is higher than the fourth glass transition temperature.

2. The polylactic acid composite material according to claim 1, wherein the substrate particle comprises at least one item selected from the group consisting of hydroxyapatite, calcium polyphosphate, and tricalcium phosphate.

3. The polylactic acid composite material according to claim 1, wherein:
a mass percentage of the substrate particle is 1 wt % to 30 wt %; and
an average particle diameter of the substrate particle is 5 nm to 200 μm.

4. The polylactic acid composite material according to claim 1, wherein the polylactic acid composite material is applied in a clinical application of human orthopedics repair.

5. The polylactic acid composite material according to claim 1, wherein the core-shell structure is uniformly dispersed in the polylactic acid matrix.

6. The polylactic acid composite material according to claim 1, wherein the substrate particle is rigid particle having a Young's modulus greater than $2 \times 10^{11}$ Pa.

7. The polylactic acid composite material according to claim 1, wherein the substrate particle is shaped as spherical, ellipsoidal, or irregularly stereoscopic.

8. The polylactic acid composite material according to claim 1, wherein the intermediate layer is maintained in a rubbery state.

9. The polylactic acid composite material according to claim 1, wherein the fourth glass transition temperature is from −37° C. to 36° C.

10. The polylactic acid composite material according to claim 1, wherein the intermediate layer is formed by modifying a surface of the substrate particle.

11. The polylactic acid composite material according to claim 1, wherein the polylactic acid matrix comprises a plurality of core-shell structures.

* * * * *